Figure 1:
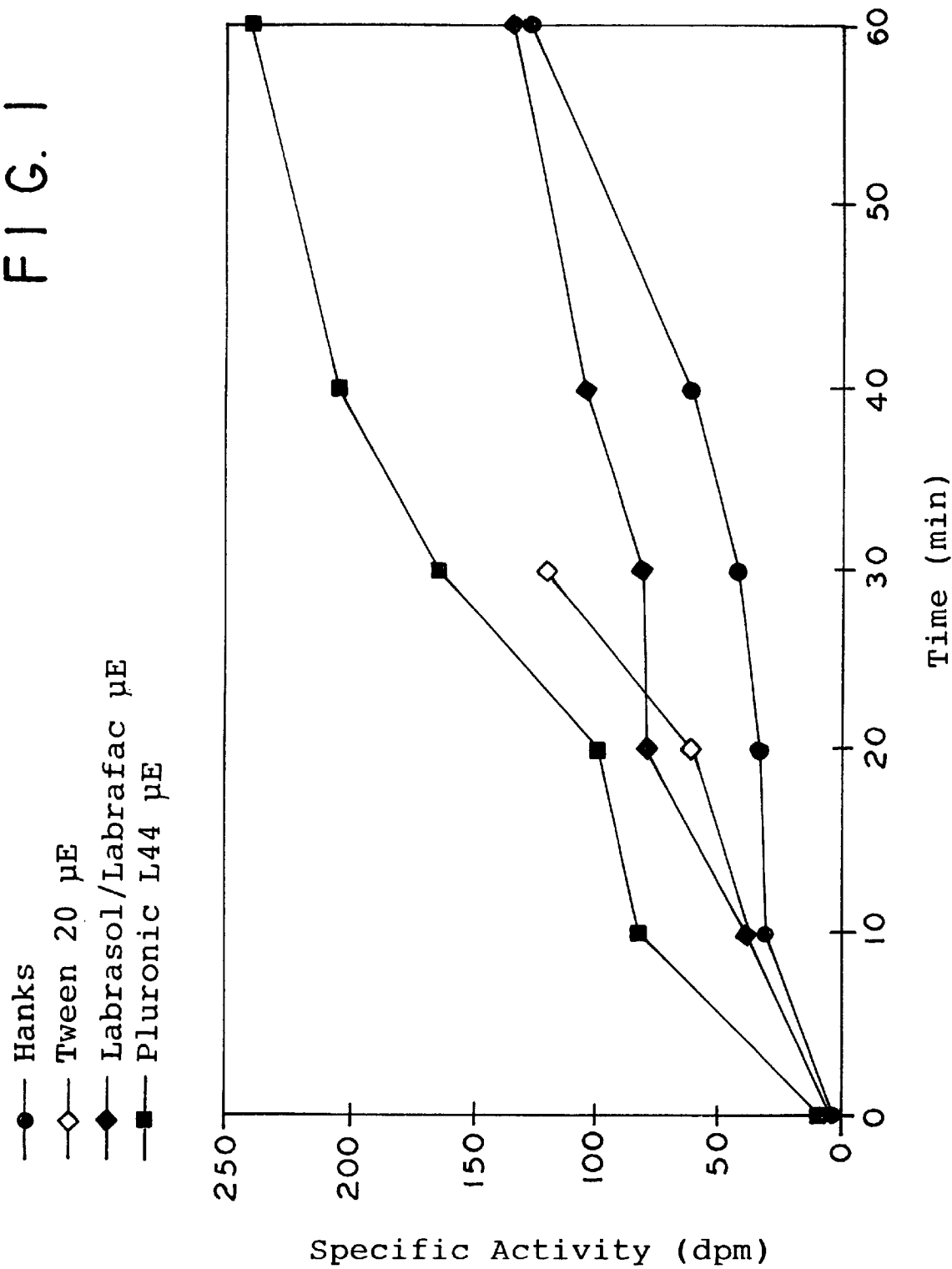

United States Patent [19]
Burnside et al.

[11] Patent Number: 5,883,103
[45] Date of Patent: *Mar. 16, 1999

[54] ORAL ACYCLOVIR DELIVERY

[75] Inventors: Beth A. Burnside, Silver Spring; Carol E. Mattes, Gaithersburg; Charlotte M. McGuinness, Rockville; Edward M. Rudnic, North Potomac; George W. Belendiuk, Potomac, all of Md.

[73] Assignee: Shire Laboratories Inc., Rockville, Md.

[ * ] Notice: The terminal 10 months of this patent has been disclaimed.

[21] Appl. No.: 475,036

[22] Filed: Jun. 7, 1995

[51] Int. Cl.$^6$ .......................... A61K 9/107; A61K 31/52
[52] U.S. Cl. .......................... 514/262; 514/938; 514/943
[58] Field of Search .................... 514/262, 938, 514/943

[56] References Cited

U.S. PATENT DOCUMENTS 5,206,219  4/1993  Desai .
5,447,729  9/1995  Belenduik et al. ...................... 424/490

OTHER PUBLICATIONS

Chemical Abstracts AN 1994:253414, Gebhard–hansen et al, WO 940528 Mar. 17, 1994.
Ritschel et al., Improvement of Peroral Absorption of Cyclosporine A by Microemulsions, *Meth.Find.Exp.Clin.Pharmacol*, 12(2):127–134, (1990).
Shichiri et al .,Increased Intestinal Absorption of Insulin in a Micellar Solution, *First Dept. of Medicine, Osaka Univ. Medical School* , pp. 175–183, (1977).
Ritschel, Microelusions for Improved Peptide Absorption from the Gastrointestinal Tract, *Meth.Find.Exp.Clin.Pharmacol.*, 13(3): 205–220, (1991).
Kararli et al., Oral Delivery of a Renin Inhibitor Compound Using Emulsion Formulations, *Pharm.Research*, vol. 9, No. 7, pp. 888–893, (1992).
Myers, et al., Systemic Bioavailability of Penclomedine (NSC–338720) from Oil–in–Water Emulsions Administrated Intraduodenally to Rats, *Int'l. Jnl. of Pharmaceutics* , 78;217–226, (1992).
Bhargava et al., Using Microemulsions for Drug Delivery, *Pharm.Tech. .*, pp. 47–51 (Mar. 1987).
Sarciaux et al., Using Microemulsion Formulations for Oral Drug Delivery of Therapeutic Peptides, *Int'l. Jnl. of Pharmaceutics*, 120:127–136, (1995).

*Primary Examiner*—Keith D. MacMillan
*Attorney, Agent, or Firm*—Elliot M. Olstein; Raina Semionow

[57] ABSTRACT

A pharmaceutical preparation for oral acyclovir delivery comprising a stable, hydrophobic emulsion comprising continuous phase of a hydrophobic material selected from the group consisting of a long chain carboxylic acid or ester or alcohol thereof dispersed in an aqueous phase or (ii) having a hydrophilic discontinuous phase dispersed in a hydrophobic phase of a long chain carboxylic acid or alcohol thereof. The emulsion with acyclovir is incorporated into a pharmaceutical carrier suitable for oral delivery.

18 Claims, 15 Drawing Sheets

ORAL ACYCLOVIR DELIVERY

The present invention relates to the field of pharmaceutical preparations of acyclovir, particularly preparations which can be administered orally.

Acyclovir has proven to be safe and effective in the treatment of herpes simplex virus (HSV), cytomegalovirus (CMV) and varicella-zoster in immunocompromised and immunocompetent patients [O'Brien, 1989]. The suppression of reactivated or newly acquired viral diseases such as genital herpes simplex or shingles for varicella-zoster as well as acute varicella-zoster infections has been achieved by oral administration of acyclovir [Spruance, 1993; Balfour, 1993]. Morbidity and mortality from viral disease have been reduced by pre- and postoperative prophylaxis with long-term (>6 months) oral acyclovir therapy [Elkins, 1993; Fletcher, 1991; Prentice, 1994; Paya, 1993]. Concurrent acyclovir and AZT(azidothymidine) therapy has extended the survival of AIDS patients by one year when acyclovir therapy was begun at time of diagnosis [Stein, 1994]. Acyclovir therapy for acute varicella-zoster disease reduces fever, chronic pain, the progression of rash and accelerates cutaneous healing {Balfour, 1993].

Acyclovir, is currently marketed as capsules (200 mg) tablets (800 mg) and suspension for oral administration [McEvoy, 1993; Barnhart, 1994]. Orally administered acyclovir is slowly and erratically absorbed with 15–30% bioavailability [O'Brien, 1989; Barnhart, 1994]. Over half the dose of the currently marketed formulation is recovered in the feces [Schaeffer, 1978]. Failure to respond to acyclovir therapy may arise from an inadequate dose (frequency of dose or total daily dose); patient noncompliance; malabsorption in the intestine; or, resistant viral strains [Mindel, 1993]. The need for readily absorbed oral antiviral agents has been identified as imperative for treatment of viral diseases to both patient populations since long term IV treatment is restrictive and compliance with oral acyclovir is difficult. [Katlama, 1993]. An acyclovir preparation for oral delivery which permitted lower dosing and less frequent administration would facilitate compliance.

The oral acyclovir preparations of the invention are designed to overcome the above failings and may be utilized, inter alia, for prophylaxis of immuno-compromised patients; suppression of latent or recurrent viral infection(s); preemptive therapy; and treatment of acute viral infections.

Accordingly, the present invention provides a pharmaceutical preparation for oral delivery of acyclovir comprising a stable hydrophobic emulsion comprising a continuous phase of a hydrophobic material selected from the group consisting of a long chain carboxylic acid, long chain carboxylic acid ester, long chain carboxylic acid alcohol and mixtures thereof and a discontinuous phase of a hydrophilic material (water-in-oil) having acyclovir therein in a dosage form suitable for oral delivery. The hydrophobic continuous phase and the hydrophilic discontinuous phase can each independently be solid, semisolid or liquid. The acyclovir is soluble in the hydrophilic material. Preferably the carrier emulsion is a microemulsion, sometimes designated herein as "µE".

In a preferred embodiment, the invention provides a pharmaceutical preparation comprising a water-in-oil emulsion, preferably a microemulsion, containing an oil phase (such as a long chain carboxylic acid or ester or alcohol thereof), a surface active agent (such as a poloxamer) and an aqueous phase containing the acyclovir. The advantage of using a water-in-oil microemulsion is that it has the ability to dissolve relatively large amounts of polar solutes in an overall oily environment, creating a system for oral delivery of active acyclovir.

The invention will now be further described by reference to a brief description of each of the accompanying drawings. The brief description and the drawings are in no way a limitation of the invention.

FIG. 1 graphically illustrates the in situ transport of acyclovir in the microemulsion formulation of Example 2. Specific activity of acyclovir in the plasma is shown as a function of time. Three microemulsion formulation (Pluronic L44, Labrasol/Labrafc CM-10 and Tween 20) and the control solution of Hank's are shown.

Figure 2:
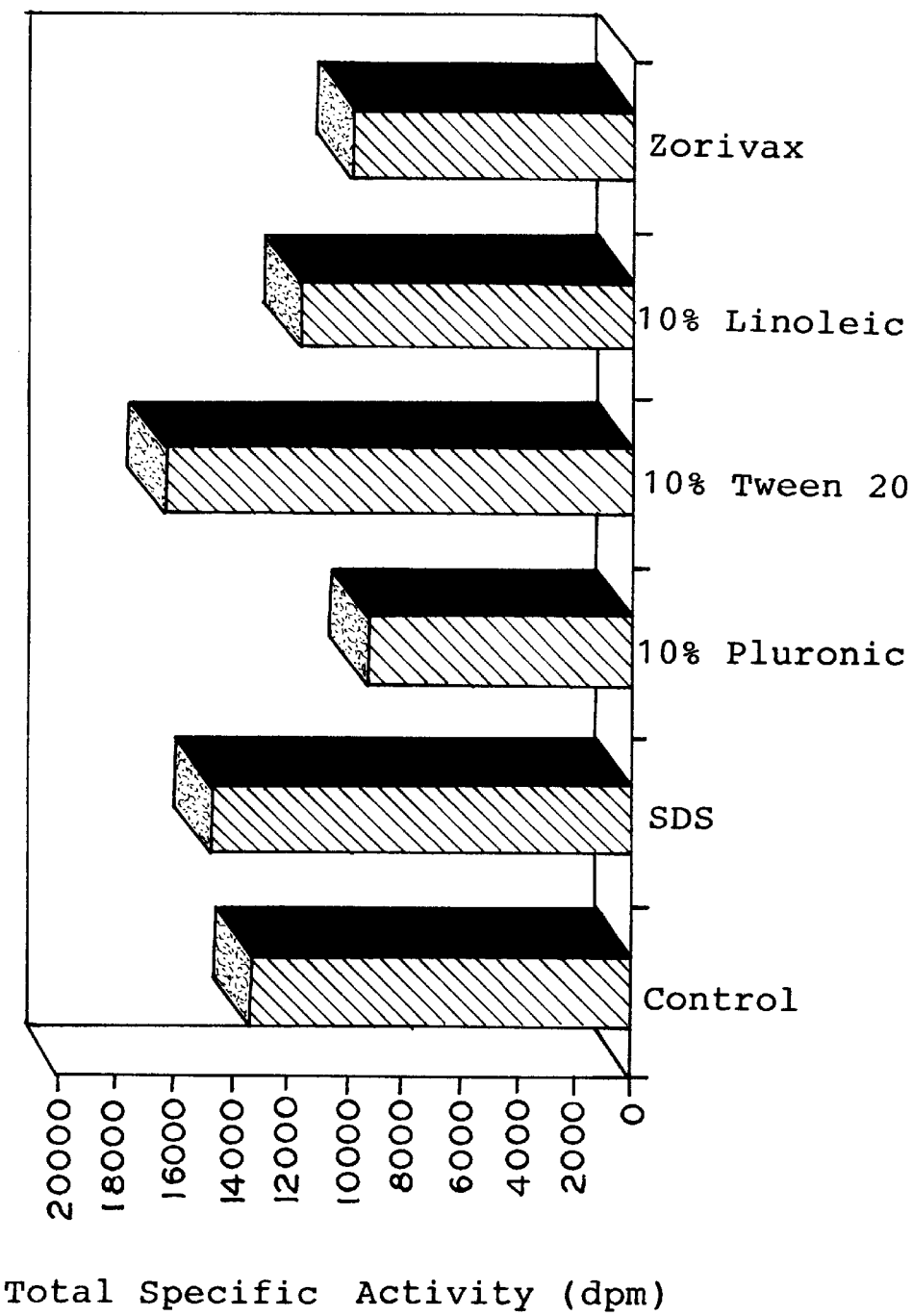

FIG. 2 graphically illustrates the in situ transport of acyclovir in solution, as described in Example 2. Acyclovir was dissolved into solutions of surfactants (SDS, Pluronic L44 and Tween 20) and oil (linoleic). Zorivaxm™ was dissolved in a balanced salt solution at the same concentration as the solutions. The specific activity of acyclovir transported per hour is shown.

Figure 3:
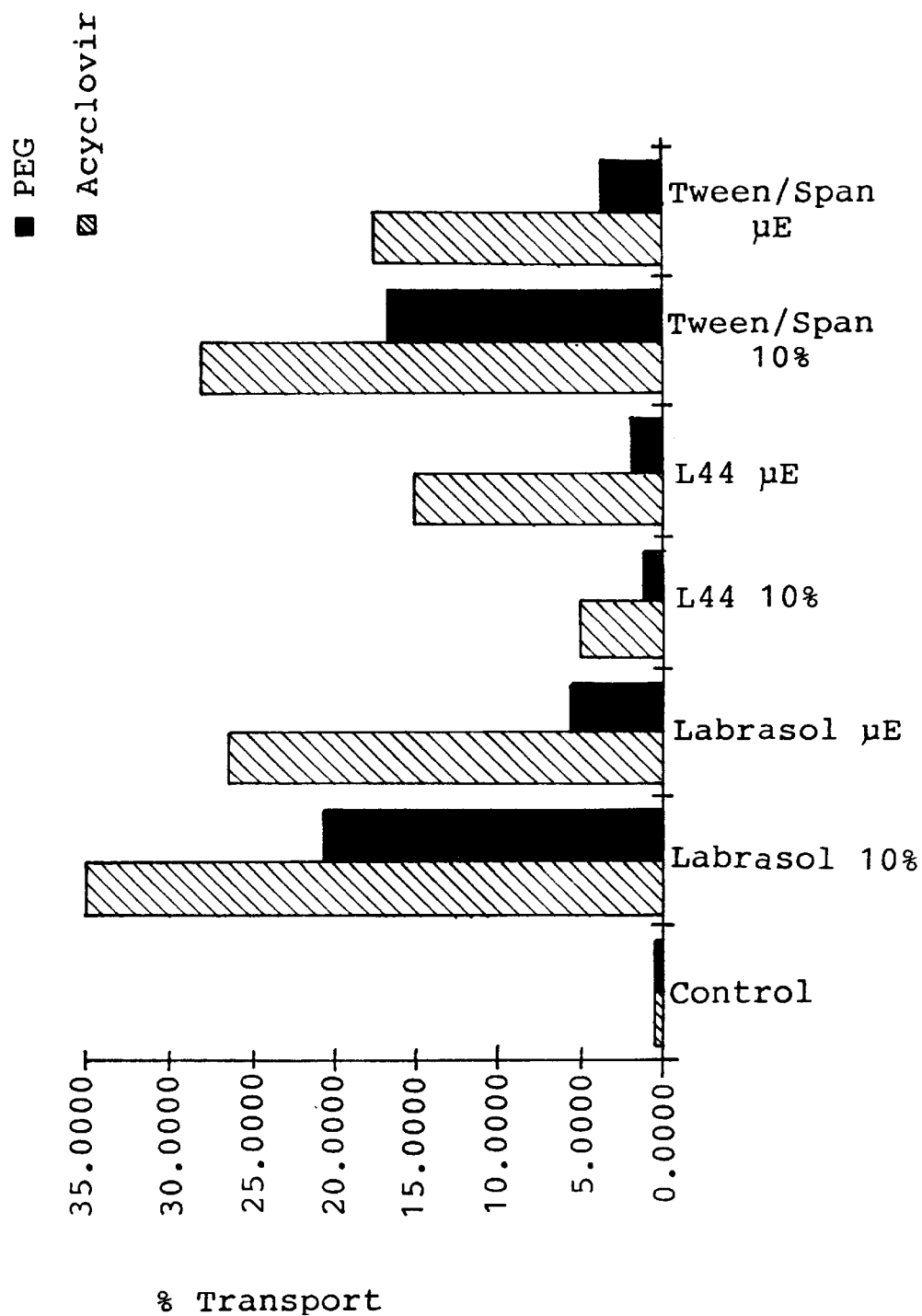

FIG. 3 graphically illustrates the increase in acyclovir transport in surfactant solutions and in microemulsions made with these surfactants as described in Example 3.

Figure 4:
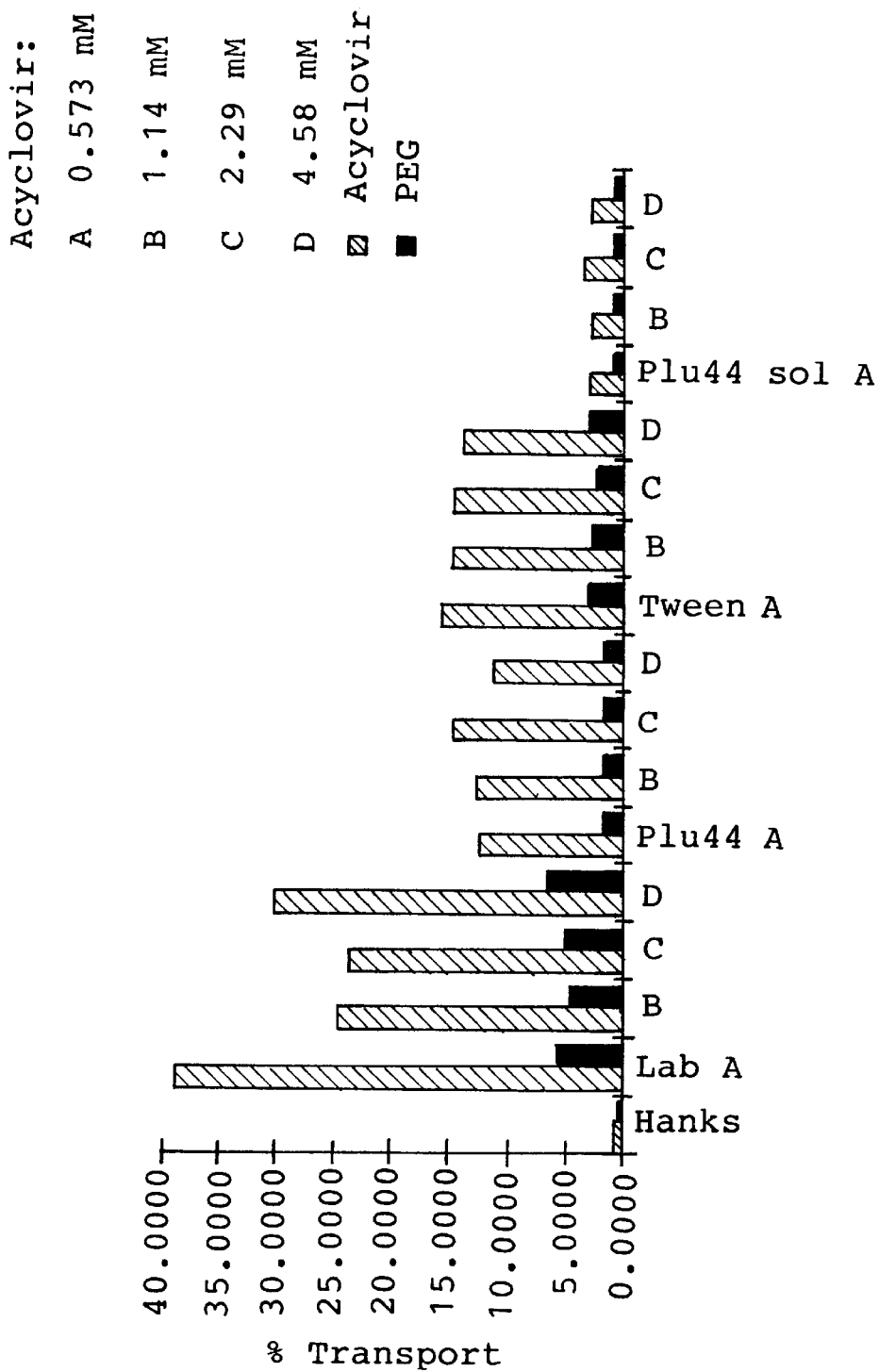

FIG. 4 graphically illustrates percent transport of acyclovir with increasing concentrations of drug in the microemulsions and L44 solutions, described in Example 4, showing that percent transport is not reduced with increasing concentration as might be the case if the mechanism were exclusively receptor mediated. Three microemulsion formulations are compared with 10% surfactant solution.

Figure 5:
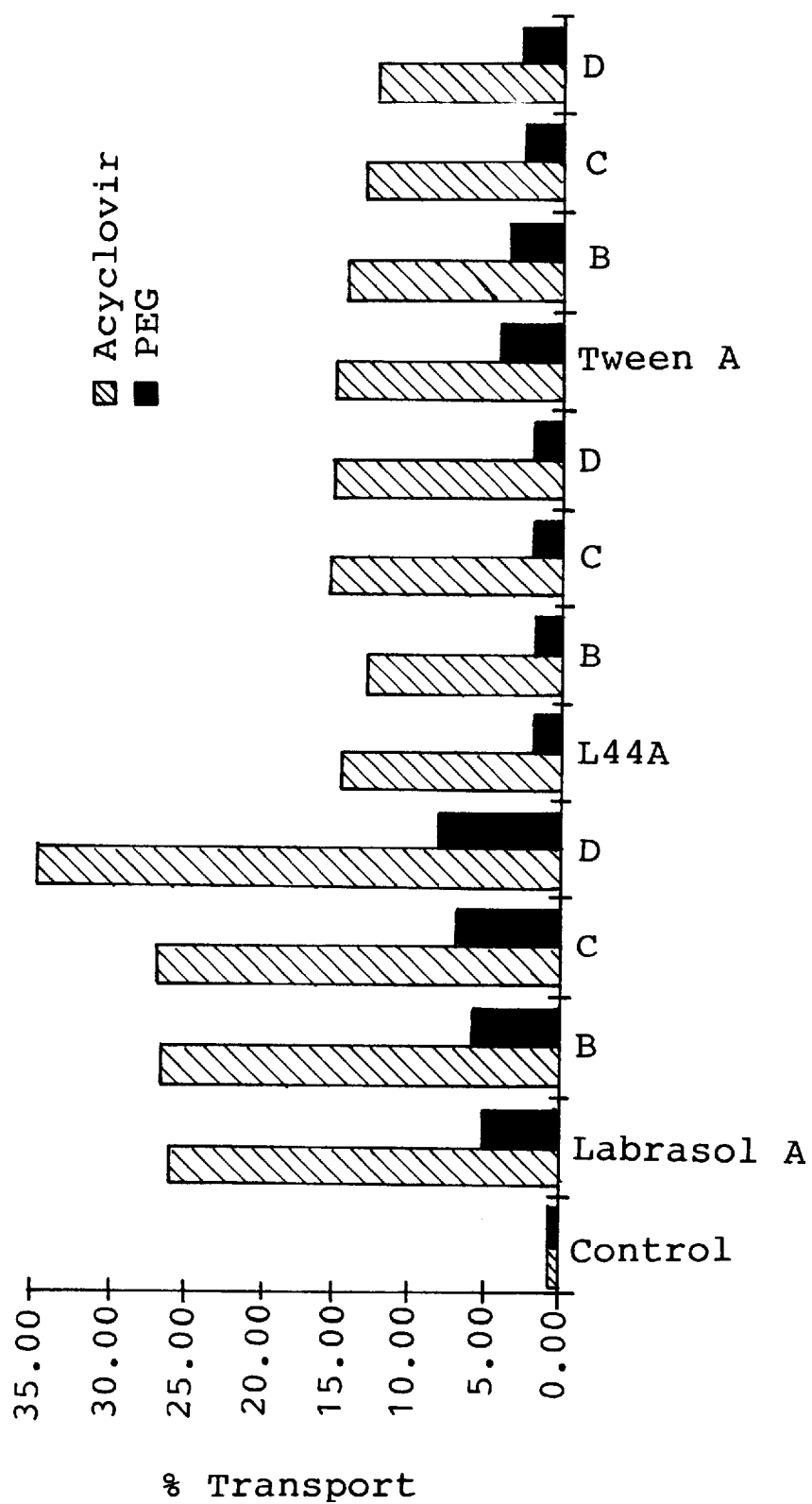

FIG. 5 graphically illustrates a confirmation of the data presented in FIG. 4 and Example 4.

Figure 6:
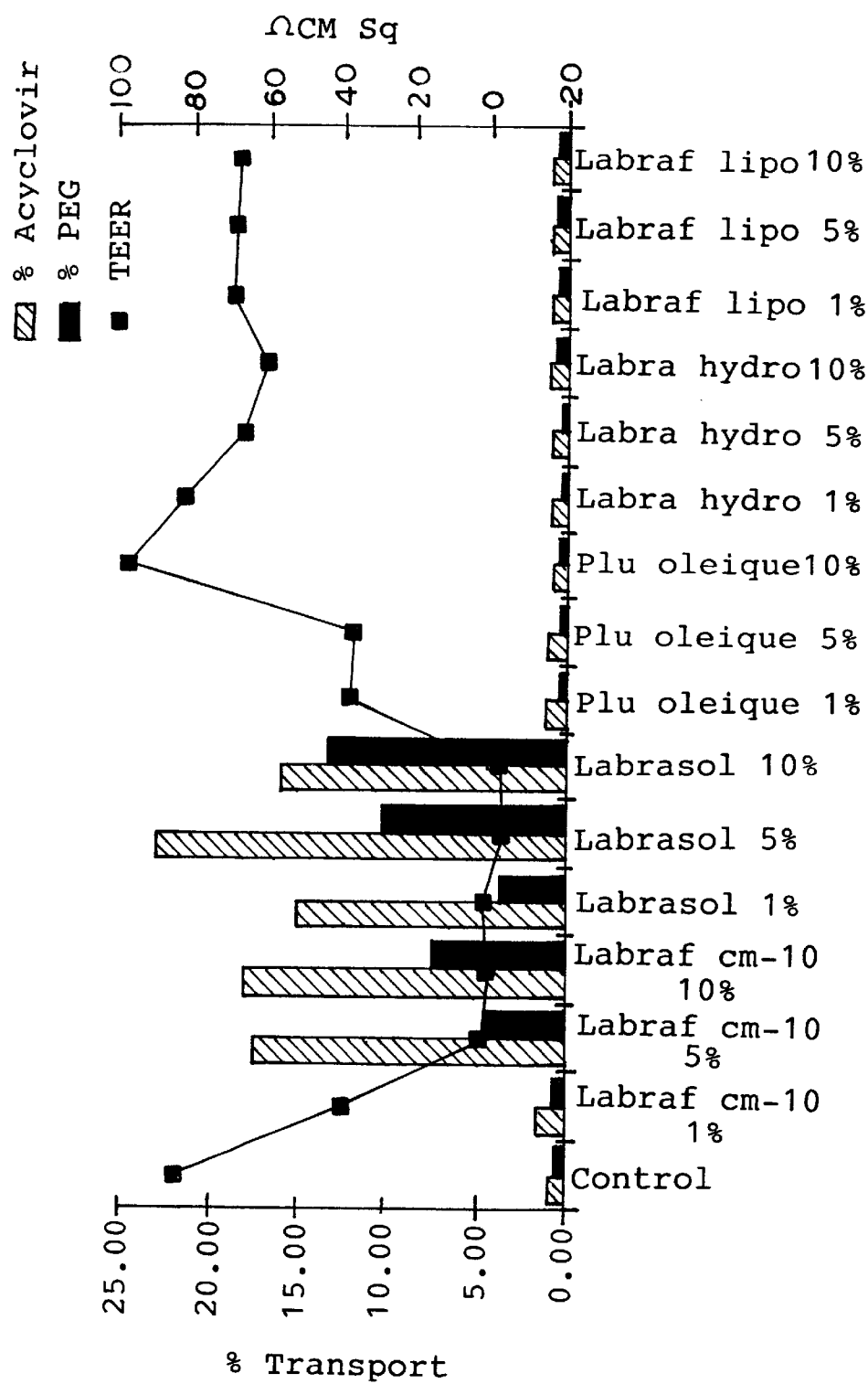

FIG. 6 graphically illustrates change in transepithelial electrical resistance (TEER) and transport with different concentrations of surfactant in HBSS solution showing that acyclovir transport is proportional to increases in membrane fluidity and can be selectively modified with different surfactants, and has reference to Example 5.

Figure 7:
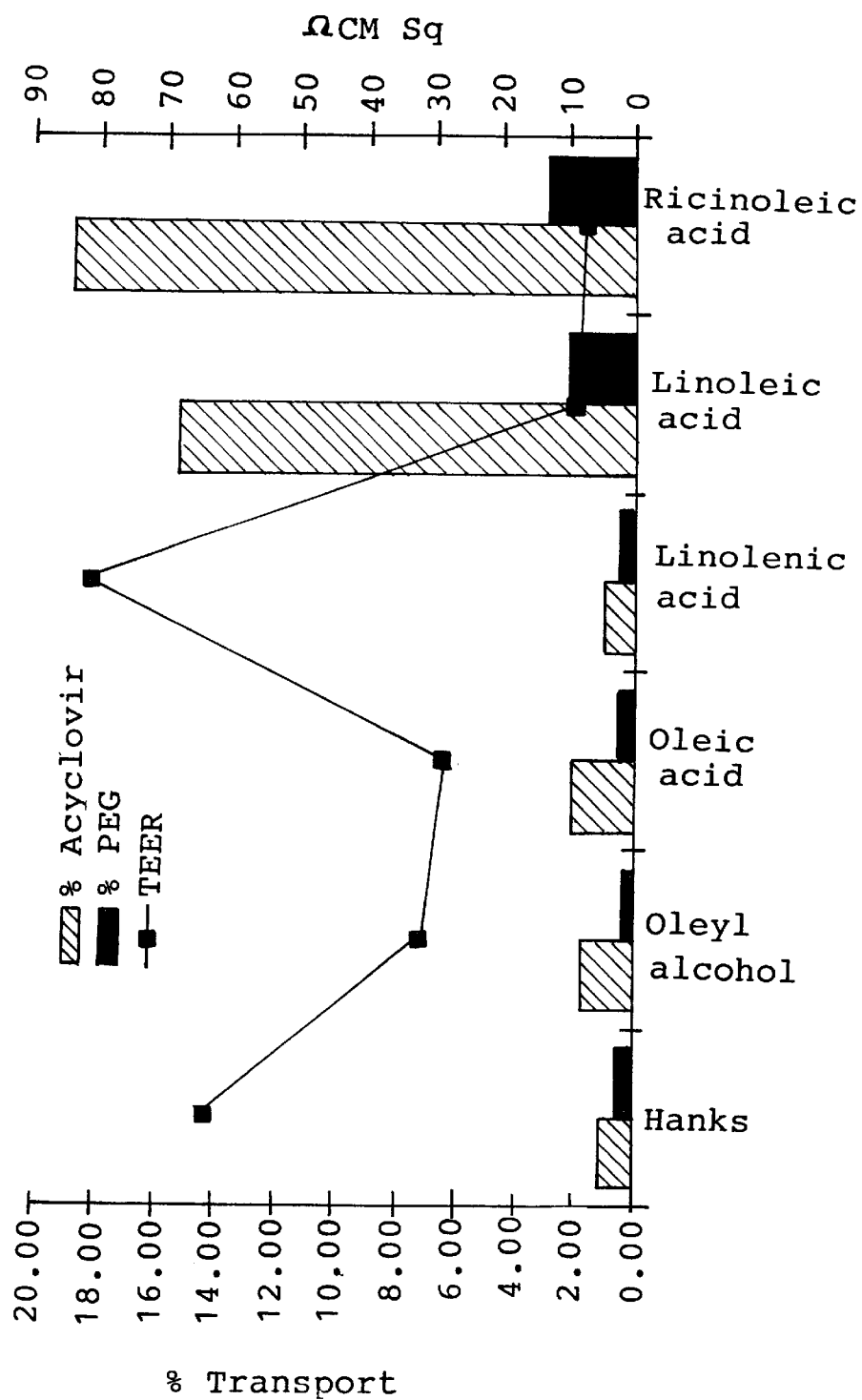

FIG. 7 graphically illustrates change in TEER and transport with different oily phases in HBSS solution showing the effect on intracellular junctions of different oily phases, and has reference to Example 6.

Figure 8:
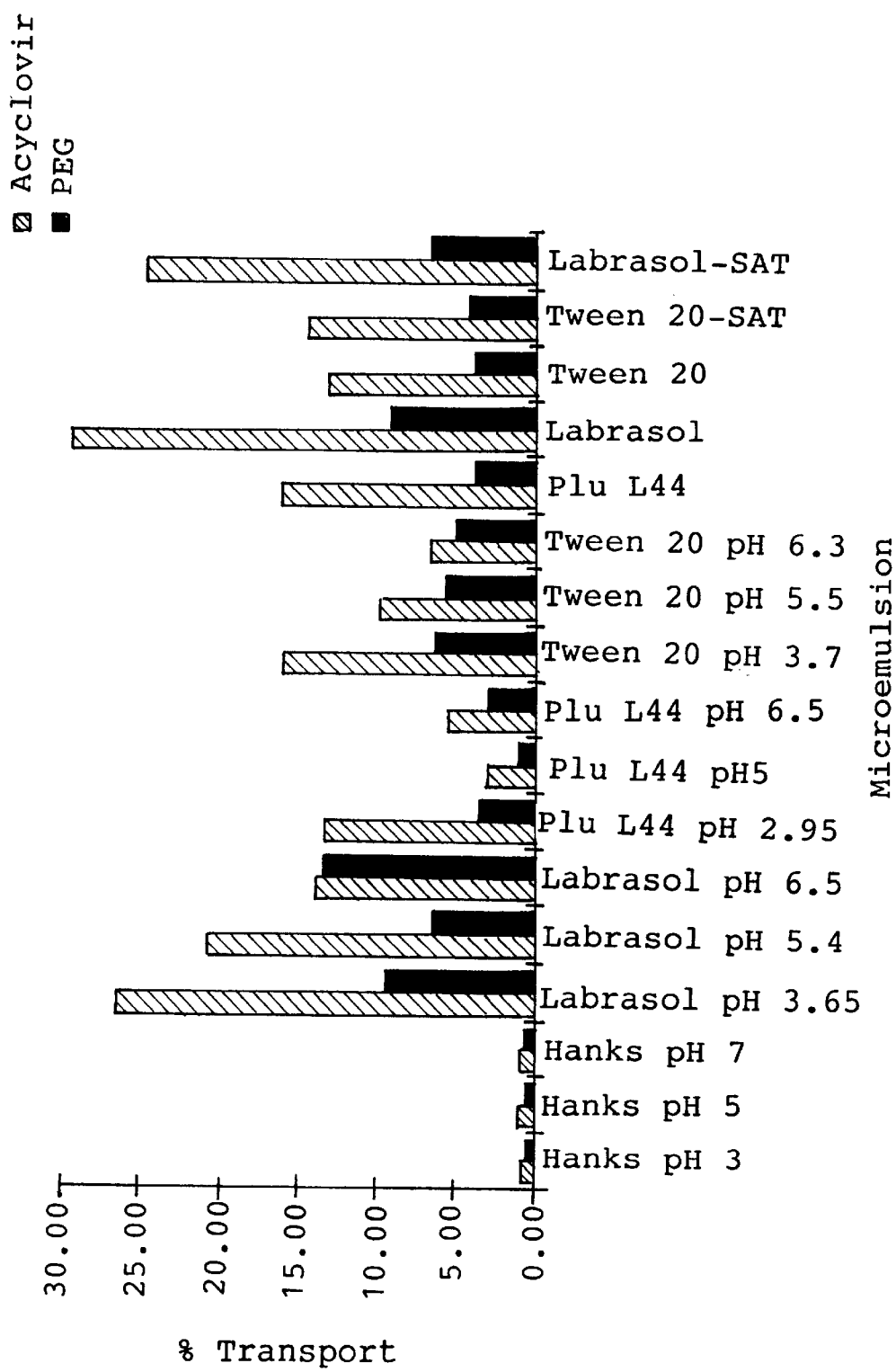

FIG. 8 graphically illustrates acyclovir transport in microemulsions showing that transport can be further increased with decreasing pH and has reference to Example 7.

Figure 9:
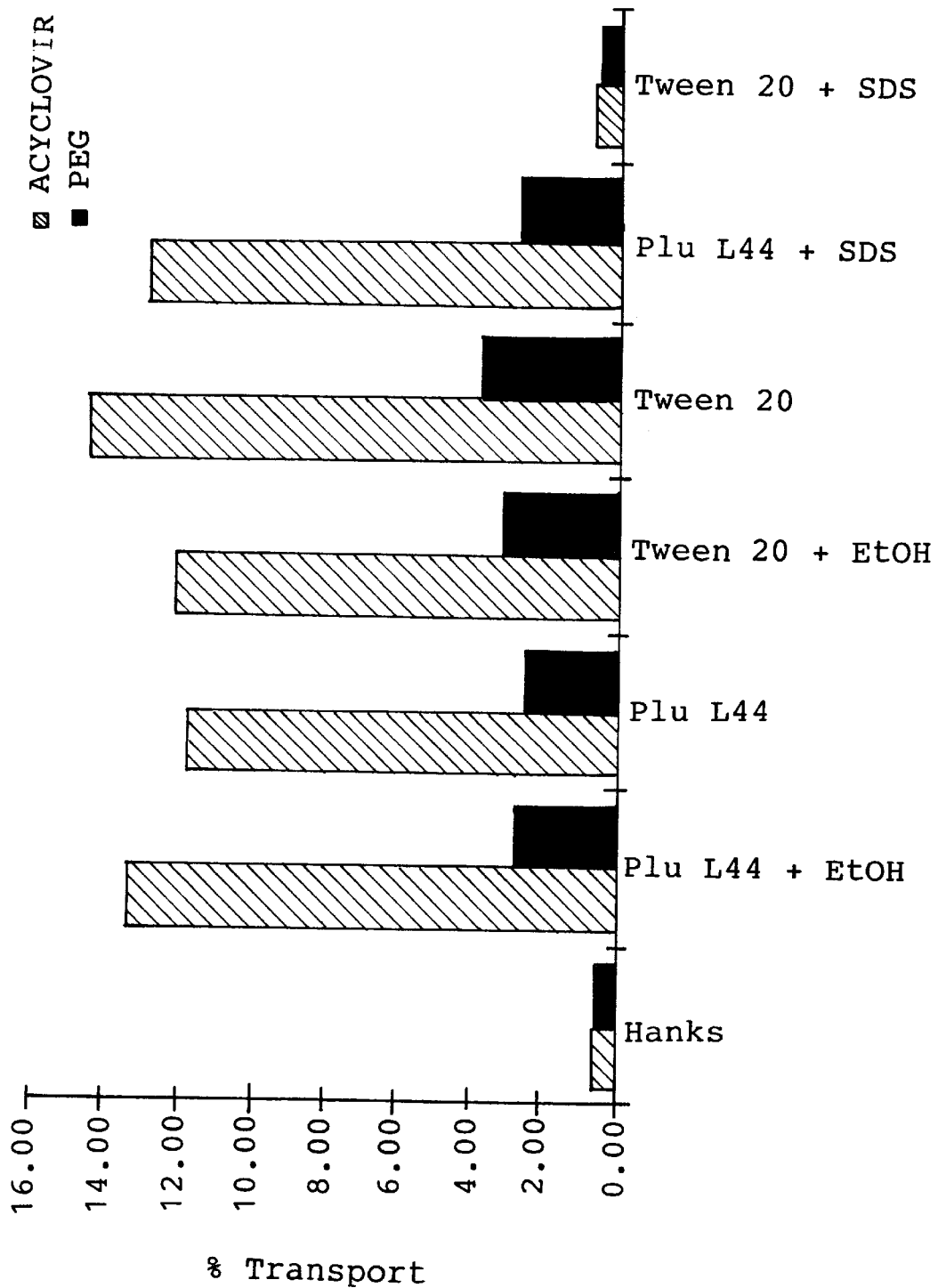

FIG. 9 graphically illustrates acyclovir transport with transport enhancing additives (EtOH, SLS, Brij 35, etc.) and has reference to Example 8.

Figure 10:
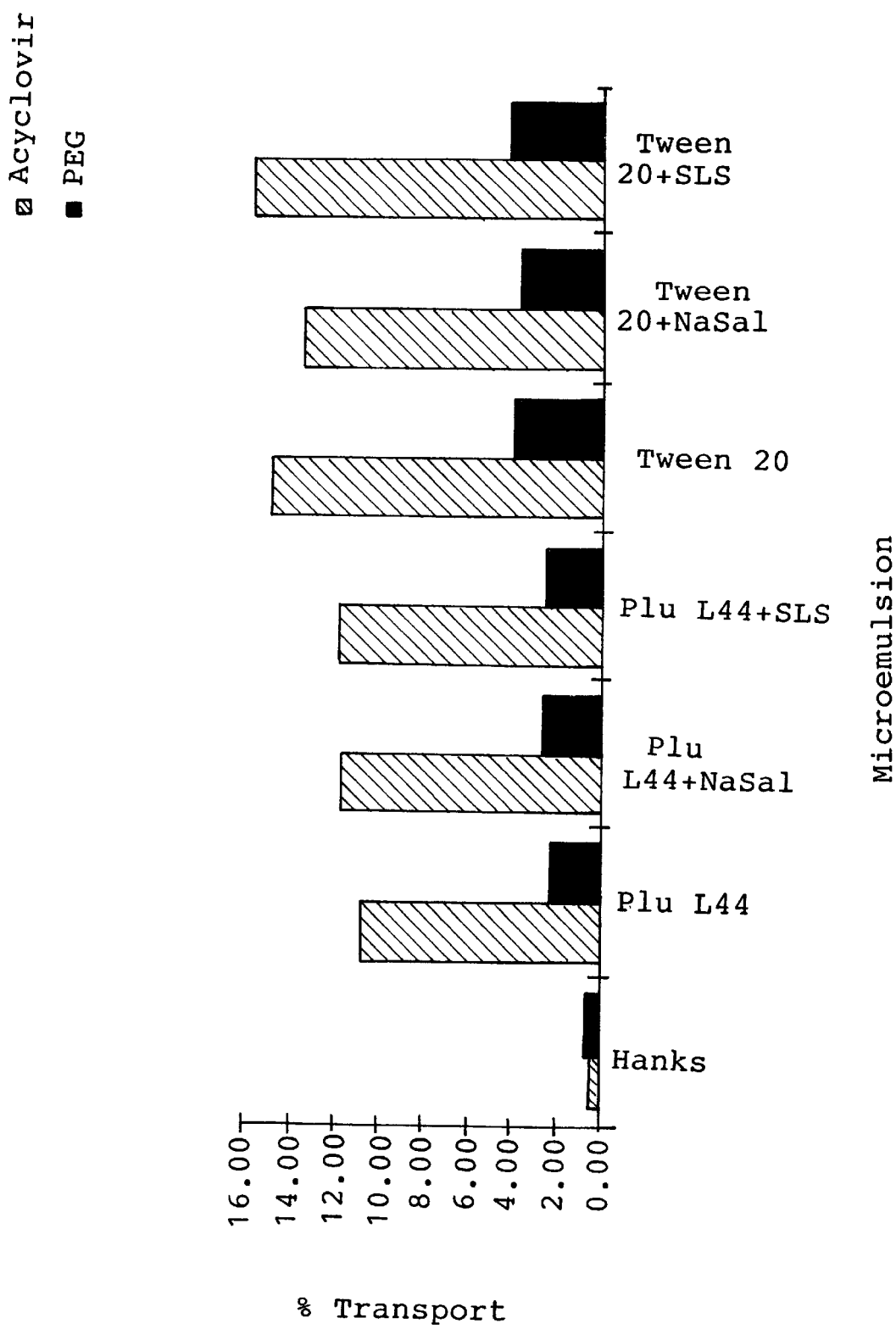

FIG. 10 graphically illustrates acyclovir transport in the presence of transport enhancers such as sodium salicylate and sodium lauryl sulfate, and has reference to Example 8.

Figure 11:
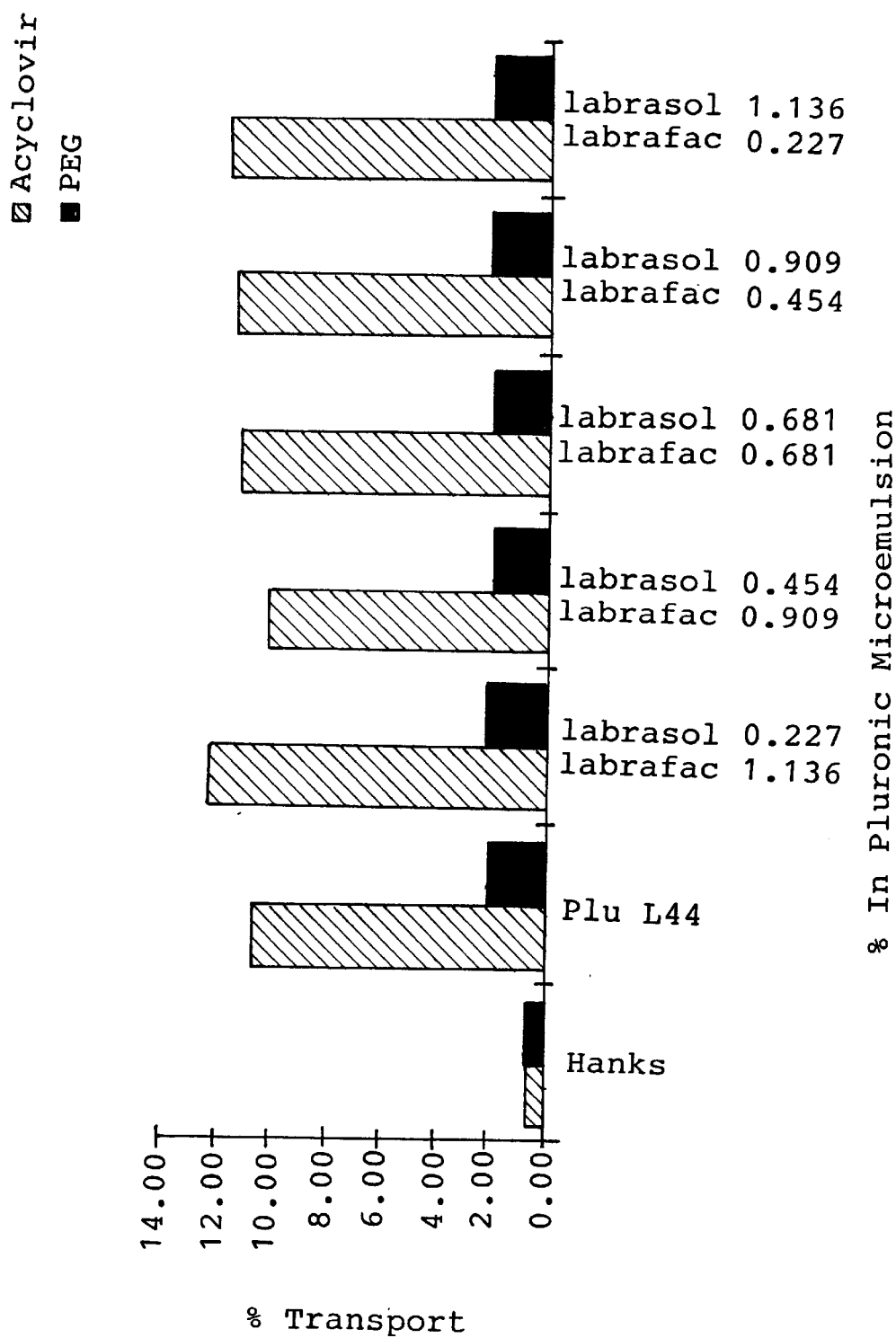

FIG. 11 graphically illustrates acyclovir transport in Pluronic L44 µE with labrasol and labrafac as co-surfactants, and has reference to Example 10.

Figure 12:
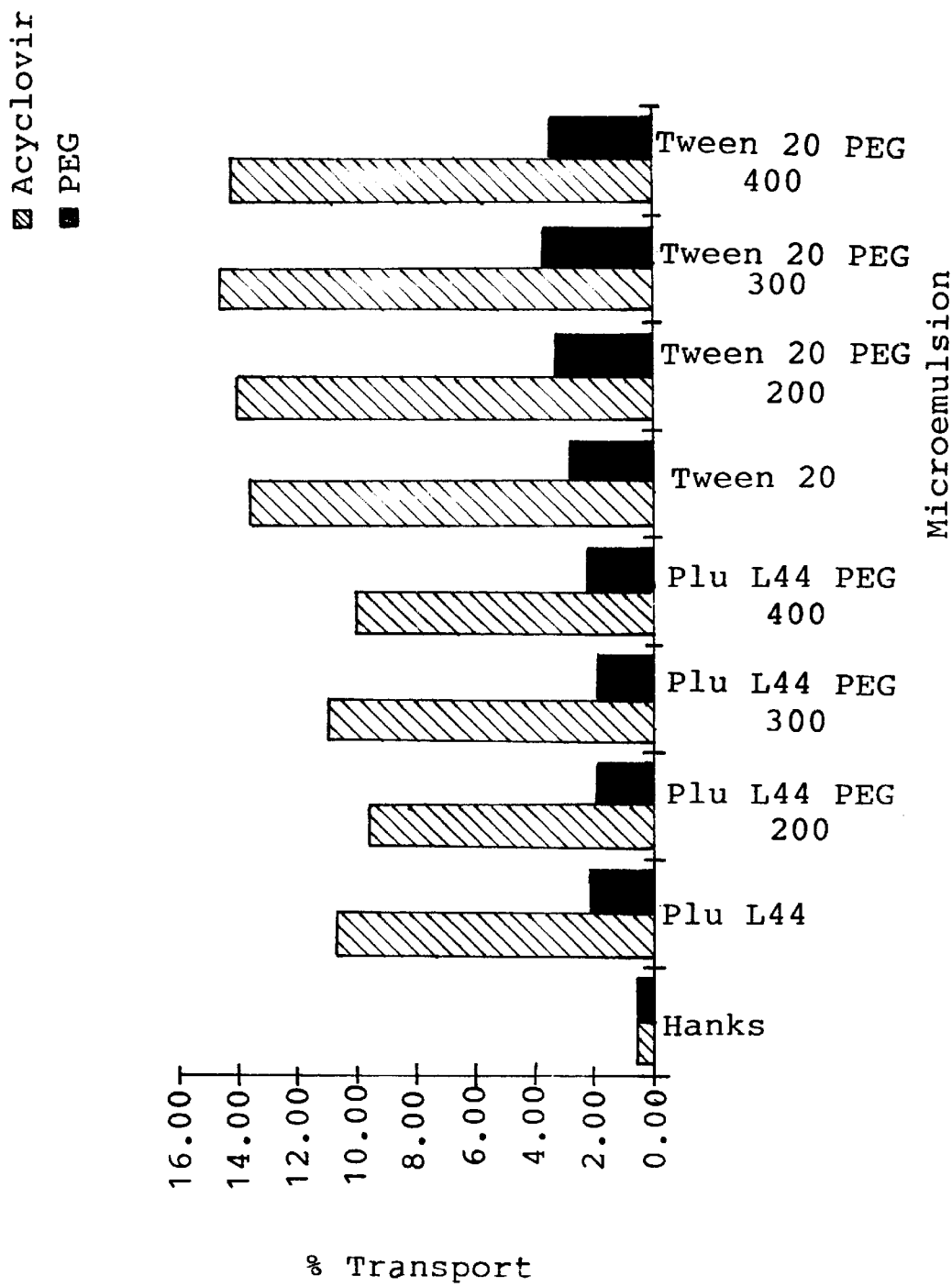

FIG. 12 graphically illustrates acyclovir transport with polyethyleneglycol (PEG)200, 300, and 400 added to the Pluronic L44 µE, and has reference to Example 11.

Figure 13:
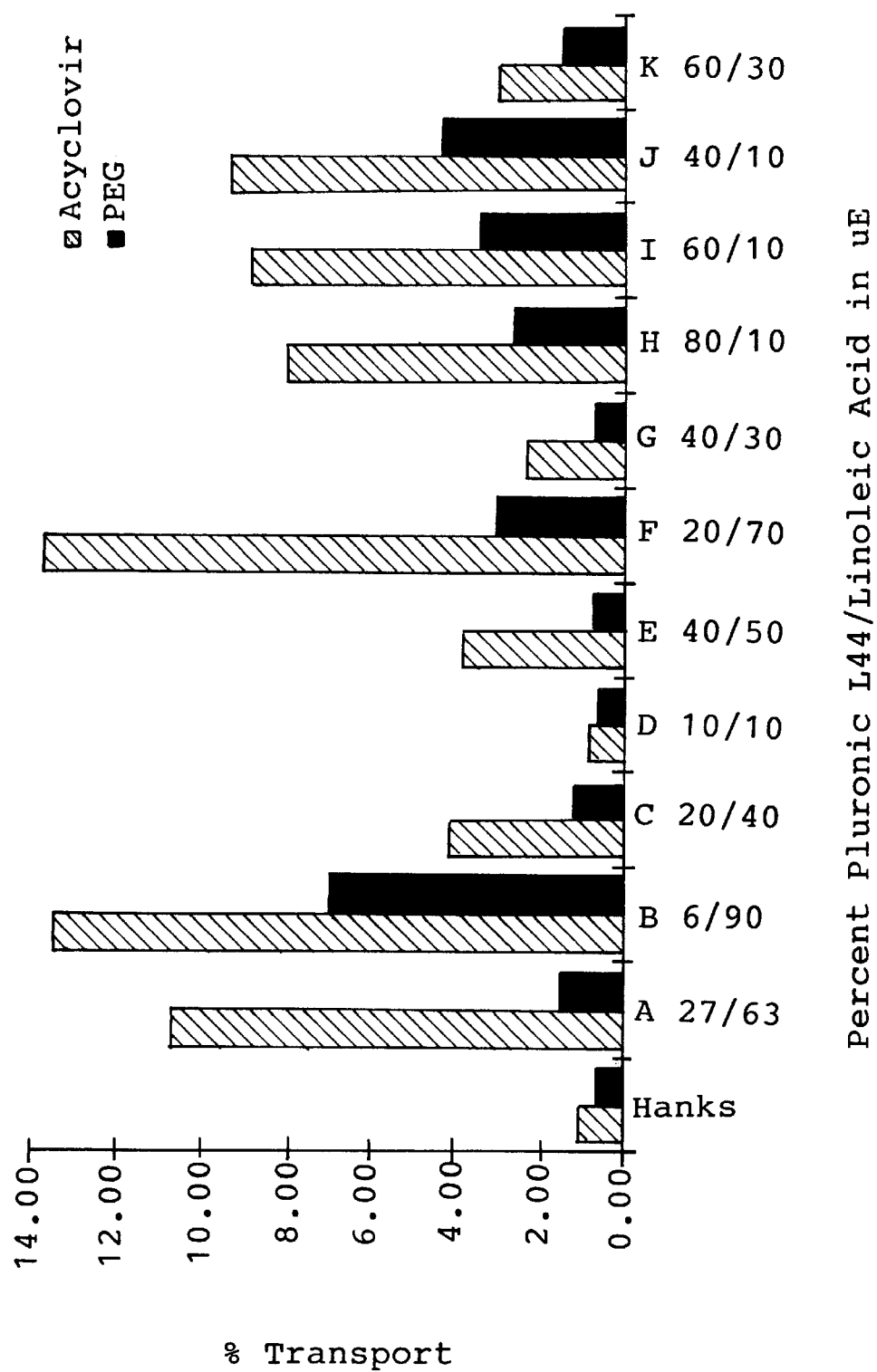

FIG. 13 graphically illustrates acyclovir transport at different points on the Pluronic L44-linoleic acid phase map demonstrating the specificity of the chosen proportions, and has reference to Example 12.

Figure 14:
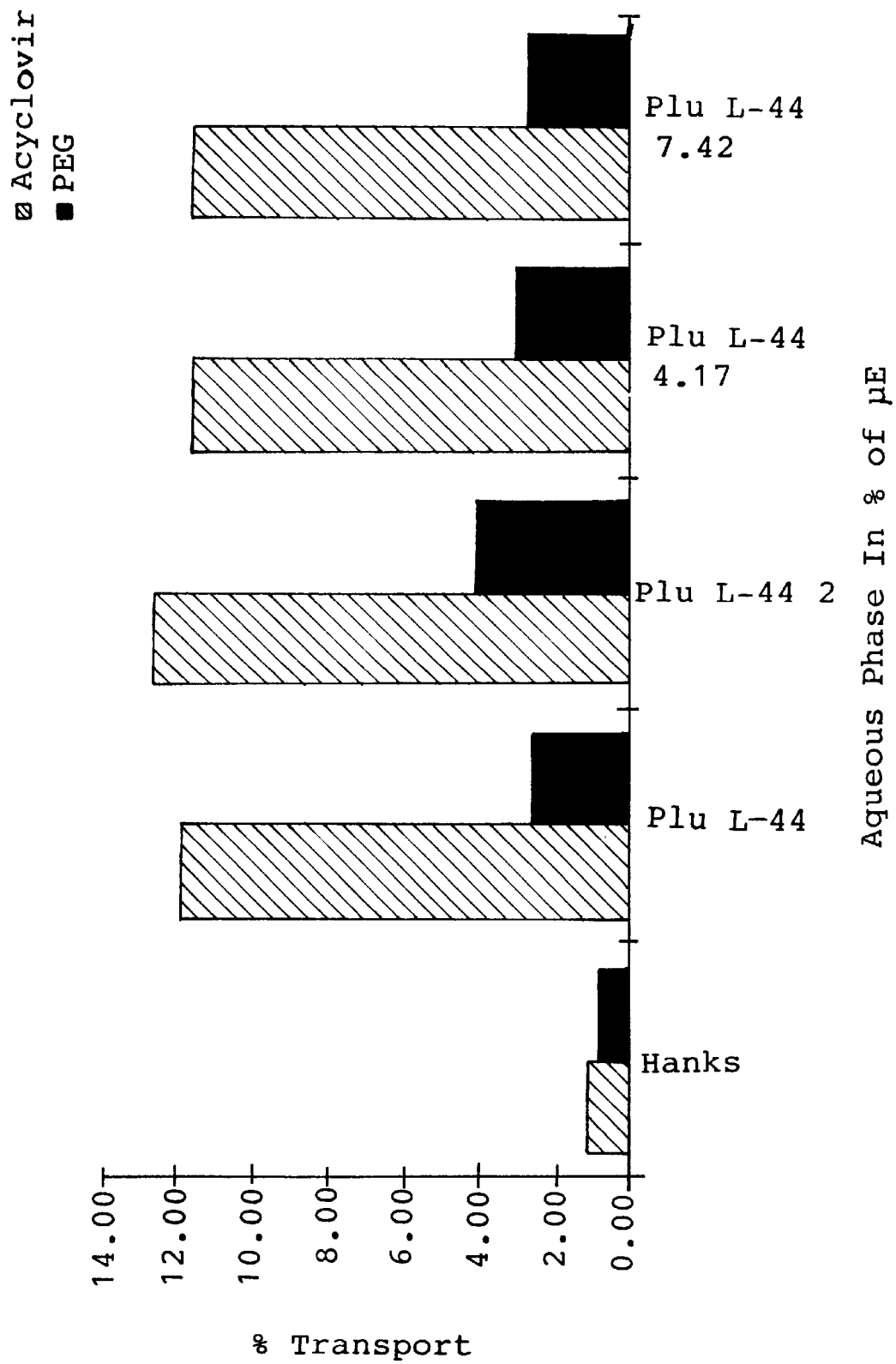

FIG. 14 graphically illustrates acyclovir transport in the presence of a gelling agent (Myverol), and has reference to Example 13.

Figure 15:
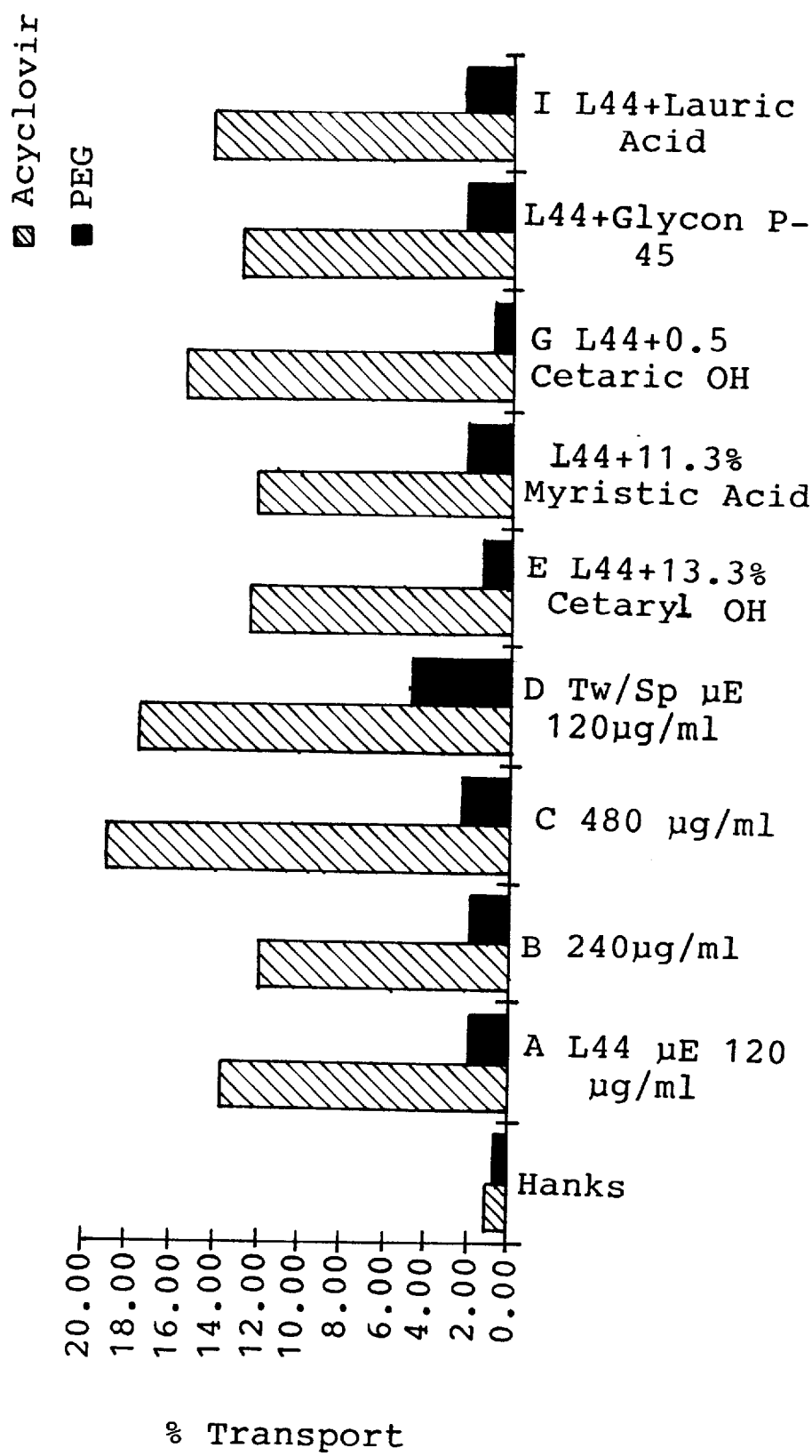

FIG. 15 graphically illustrates acyclovir transport in the presence of selected gelling agents and also has reference to Example 13.

The invention will now be described in more detail with respect to numerous embodiments and examples in support thereof.

The term "acyclovir" is used herein to refer to 2-amino-1, 9-dihydro-9-[(2-hydroxy-ethoxy) methyl]-6H-purin-6-one and the pharmaceutically acceptable salts thereof. Acyclovir is an antiviral which inhibits human herpes viruses, including herpes simplex types I (HSV-1) and 2 (HSV-2), varicella zoster, Epstein-Barr virus (EBV) and cytomegalovirus (CMV). The inhibitory activity of acyclovir is highly selective for these viruses. Acyclovir is not a substrate for the thymidine kinase (TK) expressed by uninfected normal cells. However, TK encoded by HSV, varicella zoster, and EBV converts acyclovir into acyclovir monophosphate, a nucleotide analogue. The monophosphate is further converted into diphosphate by cellular guanylate kinase and into triphosphate by a number of cellular enzymes. Acyclovir triphosphate interferes with viral DNA polymerase and to a lesser degree cellular $\alpha$-DNA polymerase. In vitro, acyclovir triphosphate is incorporated into growing chains of DNA by viral DNA polymerase and thereby terminates DNA replication. Acyclovir is preferentially taken up and selectively converted to the active triphosphate form by herpesvirus-infected cells. Thus, acyclovir is much less toxic in vitro for uninfected normal cells because less is taken up, less is converted to the active form and cellular $\alpha$-DNA polymerase is less sensitive to the effects of the active form.

An emulsion is a dispersed system containing at least two immiscible liquid phases, a hydrophobic phase and a hydrophilic phase. The emulsion comprises the dispersed phase, the dispersion phase and an emulsifying agent or surfactant agent, except when the hydrophobic material is a "self-emulsifying" ester, whereby it is possible to produce an emulsion without a separate emulsifying agent. Usually one of the two immiscible liquids is an oil while the other is aqueous. Which phase becomes the dispersed phase depends on the relative amounts of the two liquid phases and which emulsifying agent is selected. Therefore, an emulsion in which the aqueous phase is dispersed as droplets throughout the hydrophobic phase is called an water-in-oil (w/o) emulsion and vice versa. The term "colloidal" refers to emulsions in which the dispersed phase is of very fine particles, usually less than about 1 mm in size. A "microcolloid" is an emulsion wherein the dispersed particles are usually about 100 um or less in size. Cosurfactants are also common components of microcolloids and are simply surfactants included in addition to the primary surfactant.

A "microemulsion" is an optically clear, isotropic and thermodynamically stable liquid. Microemulsions are composed of an oily phase, an aqueous phase, a surfactant and, sometimes, a cosurfactant. A homogeneous mixture forms when components of the microemulsion are mixed together in any order. The resulting composition is thermodynamically stable with either a water continuous phase, an oily continuous phase, or a bicontinuous combination of the phases. Specifically, the microemulsion of the invention is a water-in-oil microemulsion, with the oil as the continuous phase.

Microemulsions are ideal for oral acyclovir delivery systems since they are homogeneous, thermodynamically stable and have uniform droplet sizes of approximately 20–40 nanometers. A water-in-oil microemulsion, in particular, has small aqueous phase droplets, uniformly dispersed in the continuous oil phase. In general, the chemical structure of acyclovir dictates that it will be at least somewhat, if not mostly, water soluble, and thus will be located inside the water droplet or very near the surface of the droplet of the water-in-oil microemulsion system. The outer oily phase of the microemulsion is able to incorporate into the intestinal cell matrix, thus creating channels (either paracellularly or transcellularly) through which the acyclovir can pass.

One general preparation procedure that maximizes acyclovir solubility is as follows: first, the acyclovir is prepared as a slurry in the aqueous phase at pH 2; second, the surfactant is added and mixed thoroughly; third, the oily phase is added and mixed to form the microemulsion. The ingredients of the microemulsion can be any of the below named surfactants, oily phases or aqueous phases.

In large-scale manufacture, these steps can be accomplished using standard mixing equipment employed in the production of ointments, creams and lotions. Specifically, mixing tanks made by Lee Industries (New Cumberland, Pa.) can be readily used. Regardless of the equipment employed, mixing needs to be accomplished using as low a shear rate as practical, in order to maintain the physical integrity of the acyclovir.

It is important to select a hydrophobic material that can erode or degrade slowly in the intestine or become incorporated into the intestinal cell matrix so that the acyclovir is released. In addition, it is possible to combine the two approaches, for example, by incorporating enteric materials in the hydrophobic phase. This would preclude the necessity of coating the capsule with an enteric polymer.

In accordance with the present invention, certain hydrophobic materials provide enhanced absorption capabilities for oral delivery of acyclovir. These materials are selected from the group consisting of long chain carboxylic acids, long chain carboxylic acid esters, long chain carboxylic acid alcohols and mixtures thereof.

Further, certain materials, when combined in accordance with the invention to form a water-in-oil microemulsion, give enhanced absorption capabilities. These materials are an oily phase, composed of long chain carboxylic acids or esters of alcohols thereof, an aqueous phase composed primarily of water and surface active agent, primarily of the non-ionic block copolymer type, that are mixed together to form a water-in-oil microemulsion.

The long chain carboxylic acids, generally contain 4–36 carbon atoms and preferably contain at least 12 carbon atoms, most preferably 12 to 22. In some cases this carbon chain is fully saturated and unbranched, while others contain one or more double bonds. They can have saturated, unsaturated, branched or straight chain hydrocarbon chains. A few contain 3-carbon rings or hydroxyl groups. The compounds are generally not surface active. They are poorly soluble in water and the longer the acid chain, the fewer the double bonds, the lower the solubility in water. The carboxylic acid group is polar and ionized at neutral pH. This accounts for the slight solubility of short-chain acids in water.

Examples of such acids are those ranging from $C_{16}$ to $C_{22}$ with up to three unsaturated bonds (also branching). Examples of saturated straight chain acids are n-dodecanoic acid, n-tetradecanoic acid, n-hexadecanoic acid, caproic acid, caprylic acid, capric acid, lauric acid, myristic acid, palmitic acid, stearic acid, arachidic acid, behenic acid, montanic acid and melissic acid. Also useful are unsaturated monoolefinic straight chain monocarboxylic acids. Examples of these are oleic acid, gadoleic acid and erucic acid. Also useful are unsaturated (polyolefinic) straight chain moncarboxylic acids. Examples of these are linoleic acid, ricinoleic acid, linolenic acid, arachidonic acid and behenolic acid. Useful branched acids include, for example, diacetyl tartaric acid.

Examples of long chain carboxylic acid esters include, but are not limited to those from the group of: glyceryl monostearates; glyceryl monopalmitates; mixtures of glyceryl monostearate and glyceryl monoalmitate (Myvaple 600, Eastman Fine Chemical Company); glyceryl monolinoleate; glyceryl monooleate; mixtures of glyceryl monopalmitate, glyceryl monostearate, glyceryl monooleate and glyceryl monolinoleate (Myverol 18-92, Eastman Fine Chemical Company); glyceryl monolinolenate; glyceryl monogadoleate; mixtures of glyceryl monopalmitate, glyceryl monostearate, glyceryl monooleate, glyceryl monolinoleate, Glyceryl monlinolenate and glyceryl monogadoleate (Myverol 18-99, Eastman Fine Chemical Company); acetylated glycerides such as distilled acetylated monoglycerides (Myvacet 5-07, 7-07 and 9-95, Eastman Fine Chemical Company); mixtures of propylene glycol monoesters, distilled monoglycerides, sodium steroyl lactylate and silicon dioxide (Myvatex TL, Eastman Fine Chemical Company); d-alpha tocopherol polyethylene glycol 1000 succinate (Vitamin E TPGS, Eastman Fine Chemical Company); mixtures of mono- and di-glyceride esters such as Atmul (Humko Chemical Division of Witco Chemical); calcium stearoyl lactylate; ethoxylated mono- and di-glycerides; lactated mono- and di-glycerides; lactylate carboxylic acid ester of glycerol and propylene glycol; lactylic esters of long chain carboxylic acids; polyglycerol esters of long chain carboxylic acids; sodium stearoyl lactylate; sorbitan monostearate; sorbitan monooleate; other sorbitan esters of long chain carboxylic acids; succinylated monglycerides; stearyl monoglyceryl citrate; stearyl heptanoate; cetyl esters of waxes; stearyl octanoate; $C_{10}$–$C_{30}$ cholesterol/lavosterol esters; and sucrose long chain carboxylic acid esters.

Examples of the self-emulsifying long chain carboxylic acid esters include those from the groups of stearates, pamitates, ricinoleates, oleates, behenates, ricinolenates, myristates, laurates, caprylates, and caproates.

The alcohols useful in the invention are exemplified by the hydroxyl forms of the carboxylic acids exemplified above.

Additives to the carboxylic acid/alcohol phase can be used to create a solid at room temperature. This addition affords the opportunity to make better use of enteric coatings. Examples of such additives are glycerol behenate, cetyl alcohol, stearic acid, sorbitan ester derivatives such as sorbitan stearate, sorbitan isostearate, polyethylene glycol 1000 to 6000, saturated polyglycolised glycerides, acrylic polymers, glyceryl monoricinoleate, palmitic acid, myristic acid, and polyvinyl acetate.

Such ingredients could be, but are not limited to, long chain carboxylic acids or esters of alcohols thereof which are paste or solid at room temperature or which, upon incorporation into the microemulsion, form a gel, such as glyceryl behenate, cetyl alcohol, stearyl alcohol, stearic acid, sodium stearate, saturated polyglycolised glycerides, acrylic polymers, myverol 18-92, myverol 18-99, myvacet 9-45, vitamin E TPGS, vitamin E-6-100, glyceryl monoricinoleate, Gelucire 44-14, palmitic acid, myristic acid, polyvinyl acetate.

Such a paste formulation is incorporated into a convenient oral dosage form of the pharmaceutical agent. One such dosage form is to incorporate the microemulsion into a gelatin capsule. The gelatin capsule can be either hard shell or soft shell. The preferred format of the invention is the soft shell gelatin capsule. The convenient oral dosage form would allow ease of swallowing and may be coated with a polymer of the enteric coating type, such that the polymer is impervious to an acidic environment like that found in the stomach, but would dissolve in a relatively basic environment like that found in the intestine.

The types of protective or sustained release coatings that can be used include, but are not limited to, ethylcellulose, hydroxypropylmethylcellulose, hydroxypropylcellulose, hydroxyethylcellulose and ester of methacrylic and ethacrylic acid (Eudragit RL, RS, and NE polymer products, Rohm Pharma, Darmstadt, Germany). The enteric protective materials or coatings can be, for example, cellulose acetate pthalate, hydroxypropylmethylcellulose pthalate, ethylvinylacetate pthalate, polyvinylacetate pthalate and esters of methacrylic and ethacrylic acid (Eudragit S, Eudragit L and Eudragit E30D, Rohm Pharma, Darmstadt, Germany).

The composition or preparation of the invention can further include a surfactant, or a mixture of two or more surfactants. A surfactant is an amphiphilic molecule consisting of a hydrophobic tail and a hydrophilic head. These molecules possess distinct regions of both hydrophilic and hydrophobic character. The hydrophobic tail can be a hydrocarbon or fluorocarbon chain of 8 to 18 carbon atoms. They are long chain molecules such as, for example, soaps or detergents. Surface active agents or surfactants are long chain molecules, such as soaps and detergents, which accumulate at the hydrophilic/hydrophobic(water/oil) interface and lower the surface tension at the interface. One effect of the reduced surface tension is the stabilization of the emulsions. This is because molecules with both polar and nonpolar groups become oriented such that the hydrocarbon tail embeds itself into the hydrophobic phase and the hydrophilic head protrudes into the hydrophilic phase. Where the hydrophobic composition or other component of the preparation includes a surface-active agent, such as a surfactant, it is usually present in amounts of about 0.05% to 50.0% weight/weight of the hydrophobic composition with a preferred range of 1.0% to 3.0% (w/w). Preferred surfactants include, for example, the Tween (polyoxyethylene sorbate) family of surfactants (ICI, Wilmington Del.), the Span (sorbitan long chain carboxylic acid esters) family of surfactants (ICI), the Pluronic (ethylene or propylene oxide block copolymers) family of surfactants (BASF, Parsippany N.J.), the Labrasol, Labrafil and Labrafac (each polyglycolyzed glycerides) families of surfactants (Gappe Fosse, St. Priest, France), sorbitan esters of oleate, stearate, laurate or other long chain carboxylic acids, poloxamers (polyethylene-polypropylene glycol block copolymers or the Pluronic brand surfactants, BASF Inc. Parsippany, N.J.), other sorbitan or sucrose long chain carboxylic acid esters, mono and diglycerides, PEG derivatives of caprylic/capric triglycerides and mixtures thereof.

Microemulsions are generally formed by adding the aqueous phase, oily phase, and surfactant to a suitable vessel and mixing. If any of the ingredient is a solid, it should be added to a liquid phase in which it is soluble and heated to dissolve. For example, if the surfactant is a solid, and it is soluble in the oily phase, then it should be dissolved completely, then followed with aqueous phase, etc. On the other hand, if the surfactant is soluble in the aqueous phase, then it should first be added to the aqueous phase, dissolved completely, followed by the oil phase. Appropriate mixing devices as mentioned above can be employed for this purpose.

The preparation of an water-in-oil emulsion based system, requires that the acyclovir be dispersed into the hydrophilic material as described above, with the hydrophobic phase being added in the presence of surfactant of self-emulsifying hydrophobic long chain carboxylic acid ester. This emulsion is then filled into a soft or hard gelatin capsule. The capsule may be further processed to provide gastric protection by enterically coating the capsule.

In accordance with the invention, acyclovir is incorporated into the microemulsions by admixture using conventional mixing devices and homogenizers used by semi-solid ointments and lotions, with agitation at speeds common to emulsified products such as creams and emulsions. Examples of common equipment employed are propeller or turbine mixers, homogenizers, colloid mills, ultrasonic mixer and microfluidizers. Examples of such brand name mixing equipment are Lee Kettle, Gaulin mixer and Stephan. The shear of the agitation should be sufficient to form a stable dispersion, but not too great to cause degradation of the acyclovir. The shear forces will form aggregates that have diameters ranging from 100–500 angstroms. Suitable homogenizers are available from Micromedics, Inc., Silverson, And APV Crepaco, Arde Barinco. Stephen and Fryma mixers can also be employed with suitable vacuum to prevent formation of bubbles. Monitoring and evaluation of pH, viscosity, specific gravity and aggregate sizes are necessary.

EXAMPLE 1

General Methodology for Transport of Acyclovir Across Caco-2 Cells Using an Acyclovir Microemulsion Formulation The following materials were used as received to prepare the acyclovir microemulsion: Pluronic L44 (BASF, Parsippany, N.J.), Linoleic acid (Emerseol 315, Emery Group, Henkle, Cincinnati, Ohio), Hank's buffer (Biofluids, Rockville, Md.). The microemulsion consists of 27.3% Pluronic L44, 63.6% Linoleic acid, and 9.95% Hank's buffer. The microemulsion was prepared with the incorporated acyclovir as follows.

A stock solution of acyclovir was prepared by adding acyclovir to Hank's buffer. The surfactant Pluronic L44 was then added and mixed thoroughly. The linoleic acid was added last. The microemulsion is assumed to have a density of 1 g/ml.

The Caco-2 cell line has been recognized as an appropriate in vitro screening model for oral drug delivery. Caco-2 cells are derived from a colon cancer and differentiate in culture to form intestinal epithelium similar to that found in the small intestine. The cells form a monolayer with many of the specific properties of the epithelial lining of the intestine: they form a brush border with normal enzymes, they form tight junctions between cells, and they acquire the barrier properties of an enterocyte sheet. When grown on permeable supports these cells can be used to screen drug microemulsion formulations.

Caco-2 colon carcinoma cells were obtained from American Type Culture Collection (Rockville, Md.) and maintained in culture in high glucose DMEM with 10% fetal calf serum, plus pen/strep, and 37° C., in 5% $CO_2$. Cells were subcultured roughly every 5–7 days, 1:3 in T75 flasks, or when cells ere 80–90% confluent, as determined by visual inspection. Caco-2 cells are adherent and were disassociated from the surface of the flask by incubation at room temperature with 0.25% trypsin in Hank's balanced salt solution (HBSS) without calcium or magnesium. Caco-2 cells are contact inhibited and when they become confluent, begin to differentiate and lose the capacity to undergo mitosis. To maintain a consistent genotype, it is important to avoid selecting from a subset of cells that is not differentiated. This is done by subculturing working stocks of cells before they differentiate.

Transport experiments used 2.45 cm Transwell cell culture inserts with 3.0 $\mu$m pores (Costar, Boston, Mass.). These are plastic inserts for tissue culture wells, which allow a distinct apical and basal compartment only connected by small pores in the growing surface. Cells are seeded on the upper surface of the insert at $3 \times 10^5$ cells per well and media changed every day. Media was changed in the lower compartments by lifting insert with a sterile forceps. The upper compartment holds 1.5 ml and the lower 2.6 ml. Tissue culture reagents were purchased from GIBCO-Life Technologies (Gaithersburg, Md.) and Biofluids (Rockville, Md.).

When cells form tight junctions, movement of liquids and ions is restricted and an electrical resistance is also formed. Electrical resistance across the cell monolayer is easily measured. Electrical resistance increases as cells differentiate with the formation of tight junctions until about day 10. When junctions are opened resistance is reduced. Resistance was measured in Caco-2 monolayers with time to monitor differentiation. Tight junctions in differentiated Caco-2 monolayers were opened with excipients and the increased transport of reference compounds was determined in cell monolayers with lowered resistance. Resistance was measured with a Millicell-ERS resistance system by placing an electrode in the upper compartment and the second in the lower compartment (Millipore, Bedford, Mass.). The monolayer resistance is determined by subtracting the resistance across cell-free transwells from the value of Caco-2 monolayer.

Transport studies used differentiated cells, which are cells that have acquired many of the characteristics of normal intestinal epithelium including a brush border and barrier properties. Initial experiments established the time course of differentiation (see below) and transport studies used cells that fell into the time frame, which these experiments ;established, of 21–28 days. A large reference molecule, polyethylene glycol (PEG) 4000, labeled with $^{14}C$, was included in transport media to verify continuity of cell monolayer.

For transport determinations, acyclovir plus transport enhancers were added to Hank's buffer, with calcium and magnesium. Transport media containing acyclovir, $^3H$-acyclovir, and $^{14}C$ PEG 4000 was added to the upper compartment of the Transwell, where the test solution was in contact with the apical surface of the cells. Transport was measured by taking aliquots from the lower compartment, which was in contact with the basal surface of the cells. Studies were performed in a six well tissue culture plate and Transwells were moved to a new well every twenty minutes giving determinations for two hours, or every thirty minutes, for a total of three hours. Aliquots were removed from each well and acyclovir levels determined by scintillation counting and HPLC. Transport was calculated as percent transport per hour from top to bottom. Determination of radioactivity were made by adding 100 microliters of sample to Aquasure (Dupont, NEN, Boston, Mass.) scintillation liquid and counting in a Wallac scintillation counter.

HPLC Assay for Acyclovir

The separation was performed using a Machery-Nagel C-18 Nucleosil HPLC Column, 5u, 4 mm×25 cm; attached to a Zorbax Rx-C-18 guard column. The acetonitrile came from Baxter (Columbia, Md.), the TFA, guanine, and guanosine were purchased from Sigma (St. Louis, Mo.), and the acyclovir came from Selog AG (Interchem Corp., Paramus, N.J.).

For an acyclovir calibration curve, acyclovir was diluted in water and serial dilutions were performed to make up solutions with acyclovir concentrations of 0.125 mg/ml to 0.00025 mg/ml.

preparation of microemulsion for HPLC analysis. The microemulsion was diluted 1:10 in 0.1N NaOH, 0.1%SDS by pipetting 0.5 ml of the microemulsion into 4.5 ml of the NaOH/SDS solution. This broke the microemulsion so that oily micelles were not injected. The microemulsion was diluted to a final dilution of 1:100 by diluting 0.5 ml of the 1:10 dilution into 4.5 ml of mobile phase A.

It was not necessary to pretreat the samples from the transport studies in Caco-2 cells as Hank's Balanced Salt solutions (HBSS) did not effect the separation of acyclovir.

A gradient is used to separate acyclovir from guanine, guansine and breakdown products. Mobile phase A consists of 0.05% TFA in water, mobile phase B is 0.05% TFA in water/acetonitrile (80:20). The gradient run is summarized in Table 1.

TABLE 1

| Time (min) | F. R. (ml/min) | 1A (%) | 1B (%) | Curve |
|---|---|---|---|---|
| 0 | 1.0 | 100 | 0 | * |
| 5 | 1.0 | 100 | 0 | 6 |
| 25 | 1.0 | 50 | 50 | 6 |
| 30 | 1.0 | 50 | 50 | 6 |
| 35 | 1.0 | 100 | 0 | 6 |

A 15 minute re-equilibration is allowed between the end of one run and the next injection.

The general methodology described in detail here was used in the acyclovir transport studies in each of Examples 3 through 13.

EXAMPLE 2

In Situ Study of Acyclovir Transport

A large group of Sprague-Dawley rats (300–350 g each) were anesthetized with urethane/chloralose (equimolar) and used in the experiments reported here as follows.

Animals are fasted overnight and then fed for 10 minutes to enhance blood flow to the mesenteric venous system before anesthetization. Body temperature is maintained at 37° C. by a heating pad and heat lamp. Exposed tissue is wrapped in saline-moistened gauze and transparent mylar film to prevent dehydration. A midline incision is made in the abdomen of the animal and approximately 10 cm of the jejeunum is exposed. The intestinal loop remains in the body cavity of the animal throughout the procedure. The upper and lower ends of the jejeunum are loosely tied with silk sutures (5-0 silk, 8 cm) at either end with care to avoid disruption of the omentum. Small incisions are made in the intestinal wall at either end of the tissue on the outer side of the sutures. The intestinal loop is lavaged with 3 milliliters of phosphate-buffered saline, pH 6.5. An angiocatheter is introduced into the mesenteric vein for sample collection at a site where first-pass metabolism and hemodilution are minimized. Prior to the introduction of the drug formulation, a blood sample (500 microliters) is drawn from the mesenteric vein that runs alongside the intestine (time=0) with 500 microliters of heparinized-saline (5% v/v) flushed into the catheter as volume replacement. One end of the intestinal loop is secured prior to the introduction of one milliliter of the acyclovir-equilibrated microemulsion or solution into the intestinal loop. The second suture is then secured. Blood (500 microliters) is drawn every 20 minutes for 2 hours and placed into an EDTA containing Vacutainer (Becton-Dickinson; 0.048 mL, 7.5% EDTA solution; 2.5 ml capacity; 13×75 mm). Samples are centrifuged for 5 minutes at room temperature in a clinical table top centrifuge. Plasma (200 microliter) is frozen prior to analysis. Packed red blood cells (resuspended to 300 microliters with saline) are returned to the animal and the catheter is flushed with 200 microliters of 5% heparin (v/v) in saline.

Separate control solutions of acyclovir were prepared in Hank's buffer and each of 10% Pluronic, 10% Tween, 10% linoleic acid and 1 mM SDS. Each contained 5 mM acyclovir and 10 $\mu$Ci [$^3$H] acyclovir was added. Microemulsions were formulated to contain approximately 4.6 mM acyclovir. Prior to introduction into the jejunal loop, 10 $\mu$Ci [$^3$H] acyclovir was added to the microemulsion. The Labrasol/Labrafac CM-10 microemulsion with a lower concentration of acyclovir and aqueous phase remained translucent, as did the microemulsions with Pluronic and Tween 20. Plasma (200 $\mu$l) was digested with tissue solubilizer (Solvable™, NEN/Dupont) prior to addition of Aquasure (Dupont, Nev.) scintillation cocktail and analysis in a Wallac scintillation counter.

From FIG. 1 it can be seen that a nearly three-fold enhancement of acyclovir transport was achieved with the Pluronic L44 microemulsion when compared to the drug in a balanced salt solution (Hank's buffer). Acyclovir transport with the Pluronic L44 microemulsion formulation was rapid and continued to increase for the one hour of monitoring while the level of transport in the control was 2- to 4-fold lower. The Labrasol/Labrafac CM-10 (Lab B) microemulsion had a 1.4-fold enhancement of acyclovir transport while the Tween 20 microemulsion components were equivalent the control solution.

FIG. 2 shows that the transport of Zorivax™ (Burroughs Wellcome) was equivalent to the pure drug in the balanced salt solution (HBSS) control. Furthermore, transport of acyclovir in solutions of surfactants or oils was not enhanced. The microemulsion formulation is required to achieve enhanced or elevated levels of acyclovir transport under physiological condition.

EXAMPLE 3

The following microemulsions further illustrate the use of Pluronic L44, Tween 20/Span 20 and Labrasol/Labrafac CM-10 microemulsions.

TABLE 2

| Ingredients | 2A (%) | 2B (%) | 2C (%) |
|---|---|---|---|
| Labrasol | 38.0 | | |
| Labrafac CM10 | 9.5 | | |
| Linoleic Acid | 47.5 | 62.9 | 47.5 |
| Pluronic L44 | | 27.0 | |
| Tween 20 | | | 42.8 |
| Span 20 | | | 4.8 |
| Aqueous | 5.0 | 10.1 | 5.0 |

Each of the above formulations can be used to provide an acyclovir pharmaceutical preparation suitable for oral delivery, using any of the acyclovir forms mentioned herein. The above formulations can be combined with acyclovir in concentrations of 1–500 mg acyclovir/ml of vehicle.

The acyclovir transport results observed across Caco-2 cells, using the microemulsions and preparations described in this example in the in vitro procedures described in detail earlier, are graphically illustrated in FIG. 3.

EXAMPLE 4

Microemulsion formulations containing Labrasol as the surfactant, Labrafac CM-10 as the cosurfactant and Hank's buffer as the aqueous phase and a variety of suitable hydrophobic phases, oleyl alcohol, oleic acid and linoleic acid can also be prepared.

The following materials are used as received to prepare the formulations: Labrasol, Labrafac CM-10 (Gattefose Corp., Westwood, N.J.), oleyl alcohol (Jannsen Chemical Green Belgium), Linoleic acid (Emersol 315, Henkel) and oleic acid (Emersol 221, Henkel).

TABLE 3

| Ingredients | 3A (%) | 3B (%) | 3C (%) | 3D (%) |
|---|---|---|---|---|
| Aqueous | 4.58 | 4.58 | 4.58 | 4.58 |
| Labrafac CM10 | 9.54 | 9.54 | 9.54 | 9.54 |
| Labrasol | 38.17 | 38.17 | 38.17 | 38.17 |
| Linoleic Acid | 47.7 | 47.7 | 47.7 | 47.7 |
| Acyclovir (mg/ml) | 0.13 | 0.26 | 0.52 | 1.01 |

Microemulsions system formulations containing Pluronic L44 as the surfactant, Hank's buffer as the aqueous phase and linoleic acid and the oily phase. The following samples contain increasing amounts of acyclovir.

TABLE 4

| Ingredients | 4A (%) | 4B (%) | 4C (%) | 4D (%) |
|---|---|---|---|---|
| Aqueous | 9.9 | 9.9 | 9.9 | 9.9 |
| Pluronic L44 | 27.0 | 27.0 | 27.0 | 27.0 |
| Linoleic Acid | 63.1 | 63.1 | 63.1 | 63.1 |
| Acyclovir (mg/ml) | 0.12 | 0.24 | 0.48 | 0.96 |

The following materials are used as received to prepare formulations: Polysorbate 20, (Tween 20, 60, 80, ICI Surfactants Wilmington, Del.); linoleic acid (Emersol 315, Henkel), Sorbitan monolaurate (Span 20, ICI, Wilmington, Del.).

TABLE 5

| Ingredients | 5A (%) | 5B (%) | 5C (%) | 5D (%) |
|---|---|---|---|---|
| Aqueous | 4.58 | 4.58 | 4.58 | 4.58 |
| Tween 20 | 42.9 | 42.9 | 42.9 | 42.9 |
| Span 20 | 4.8 | 4.8 | 4.8 | 4.8 |
| Linoleic Acid | 47.7 | 47.7 | 47.7 | 47.7 |
| Acyclovir (mg/ml) | 0.13 | 0.26 | 0.52 | 1.03 |

The following solutions were compared to microemulsion formulations:

TABLE 6

| Ingredients | 6A (%) | 6B (%) | 6C % | 6D (%) |
|---|---|---|---|---|
| Pluronic L44 | 24.9 | 24.9 | 24.8 | 24.5 |
| Aqueous | 75.1 | 75.1 | 75.2 | 75.2 |
| Acyclovir (mg/ml) | 0.13 | 0.26 | 0.53 | 1.05 |

Each of the above formulations can be used to provide an acyclovir pharmaceutical preparation suitable for oral delivery, using any of the acyclovir forms mentioned herein. The above formulations can be modified to deliver acyclovir in concentrations of 1–250 mg acyclovir/ml of vehicle.

The acyclovir transport results observed across Caco-2 cells, using the microemulsions and preparations described in this example in the in vitro procedures described in detail earlier, are graphically illustrated in FIGS. 4 and 5.

EXAMPLE 5

This example lists surfactants in Hank's buffer containing acyclovir used in transport studies in comparison to Pluronic L44 microemulsions prepared at 1, 5 and 10% surfactant. The surfactants examined were Labrafac CM 10, Labrasol, Plurol Oleique, Labrafac Hydro, Labrafac Lipo, Aqueous.

Each of the above formulations can be used to provide an acyclovir pharmaceutical preparation suitable for oral delivery, using any of the acyclovir forms mentioned herein. The above formulations can be combined with acyclovir in concentrations of 1–250 mg acyclovir/ml of vehicle.

The acyclovir transport results observed across Caco-2 cells, using the microemulsions and preparations described in this example, in the in vitro procedures described in detail earlier, are graphically illustrated in FIG. 6. Decreased transepithelial resistance correlates with enhanced transport.

EXAMPLE 6

The following example lists solutions of fatty acids in Hank's buffer at 40 mM.

The acyclovir transport results observed across Caco-2 cells, using the microemulsions and preparations described in this example in the in vitro procedures described in detail earlier, are graphically illustrated in FIG. 7. Decreased transepithelial resistance correlates with enhanced transport.

EXAMPLE 7

The following tables lists three microemulsions over the pH range of 3–6.50. The pH of the formulations was adjusted using 10N NaOH.

TABLE 7

| Ingredient | 7A (%) | 7B (%) | 7C (%) | 7D (%) | 7E (%) | 7F (%) |
|---|---|---|---|---|---|---|
| Aqueous | 9.9 | 4.7 | 4.9 | 9.9 | 4.5 | 4.5 |
| Pluronic L44 | 27 | | | 27 | | |
| Linoleic Acid | 63.1 | 47.4 | 47.1 | 63.1 | 47.8 | 47.7 |
| Tween 20 | | | 43.2 | | 42.9 | |
| Span 20 | | | 4.8 | | 4.8 | |
| Labrafac CM 10 | | 9.5 | | | | 9.5 |
| Labrasol | | 38.4 | | | | 38.3 |

Each of the above formulations can be used to provide an acyclovir pharmaceutical preparation suitable for oral delivery, using any of the acyclovir forms mentioned herein. The above formulations can be combined with acyclovir in concentrations of 1–250 mg acyclovir/ml of vehicle.

The acyclovir transport results observed across Caco-2 cells, using the microemulsions and preparations described in this example in the in vitro procedures described in detail earlier, are graphically illustrated in FIG. 8.

EXAMPLE 8

The example demonstrates the inclusion of ethanol as part of the aqueous phase and also the inclusion of a water soluble surfactant, sodium lauryl sulfate (SLS).

TABLE 8

| Ingredient | 8A(%) | 8B(%) | 8C(%) | 8D(%) | 8E(%) | 8F(%) |
|---|---|---|---|---|---|---|
| Ethanol | 3.8 | | 1.2 | | | |
| Aqueous | 6.1 | 9.9 | 3.6 | 4.8 | 3.9 | 9.0 |
| Pluronic L44 | 27.0 | 27.0 | | | | 27.0 |
| Linoleic Acid | 63.1 | 63.1 | 47.6 | 47.6 | 47.6 | 63.1 |
| Tween 20 | | | 42.9 | 42.9 | 42.9 | |

TABLE 8-continued

| Ingredient | 8A(%) | 8B(%) | 8C(%) | 8D(%) | 8E(%) | 8F(%) |
|---|---|---|---|---|---|---|
| Span 20 | | | 4.8 | 4.8 | 4.8 | |
| Sodium Lauryl Sulfate | | | | | .9 | .9 |

Each of the above formulations can be used to provide an acyclovir pharmaceutical preparation suitable for oral delivery, using any of the acyclovir forms mentioned herein. The above formulations can be combined with acyclovir in concentrations of 1–250 mg acyclovir/ml of vehicle.

The acyclovir transport results observed across Caco-2 cells, using the microemulsions and preparations described in this example in the in vitro procedures described in detail earlier, are graphically illustrated in FIG. 9.

EXAMPLE 9

This example illustrates the addition of water soluble surfactants sodium lauryl sulfate (SLS) and sodium salicylate (Na-Sal) to the Pluronic L44 and Tween 20/Span 20 microemulsions containing linoleic acid as the oily phase and Hank's buffer as the aqueous phase.

TABLE 9

| Ingredient | 8A(%) | 8B(%) | 8C(%) | 8D(%) | 8E(%) | 8F(%) |
|---|---|---|---|---|---|---|
| Aqueous Phase | 9.0 | 3.8 | 9.0 | 3.8 | 9.0 | 3.8 |
| Pluronic L44 | 27.0 | | 27.0 | | 27.0 | |
| Linoleic Acid | 63.1 | 47.6 | 63.1 | 47.6 | 63.1 | 47.6 |
| Tween 20 | | 42.9 | | 42.9 | | 42.9 |
| Span 20 | | 4.8 | | 4.8 | | 4.8 |

Each of the above formulations can be used to provide an acyclovir pharmaceutical preparation suitable for oral delivery, using any of the acyclovir forms mentioned herein. The above formulations can be combined with acyclovir in concentrations of 1–250 mg acyclovir/ml of vehicle.

The acyclovir transport results observed across Caco-2 cells, using the microemulsions and preparations described in this example in the in vitro procedures described in detail earlier, are graphically illustrated in FIG. 10.

EXAMPLE 10

The following microemulsion contains a combination of surfactants Pluronic L44 and Labrasol and a cosurfactant Labrafac CM-10 in combination with linoleic acid and Hank's buffer as the aqueous phase.

TABLE 10

| Ingredients | 10A(%) | 10B(%) | 10C(%) | 10D(%) | 10E(%) |
|---|---|---|---|---|---|
| Aqueous Phase | 9.1 | 9.1 | 9.1 | 9.1 | 9.1 |
| Labrasol | 0.2 | 0.45 | 0.68 | 0.9 | 1.14 |
| Labrafac CM-10 | 1.14 | 0.9 | 0.68 | 0.45 | 0.21 |
| Pluronic L44 | 25.9 | 25.9 | 25.9 | 25.9 | 25.9 |
| Linoleic Acid | 63.6 | 63.6 | 63.6 | 63.6 | 63.6 |
| Acyclovir (mg/ml) | 120 | 120 | 120 | 120 | 120 |

Each of the above formulations can be used to provide an acyclovir pharmaceutical preparation suitable for oral delivery, using any of the acyclovir forms mentioned herein. The above formulations can be modified to contain acyclovir in concentrations of 1–250 mg acyclovir of vehicle.

The acyclovir transport results observed across Caco-2 cells, using the microemulsions and preparations described in this example in the in vitro procedures described in detail earlier, are graphically illustrated in FIG. 11.

EXAMPLE 11

This example illustrates formulations where a water soluble additive is included in the aqueous phase.

TABLE 11

| Ingredient | 11A(%) | 11B(%) | 11C(%) |
|---|---|---|---|
| Aqueous Phase | 4.7 | 4.7 | 4.7 |
| PEG 200 | 0.05 | | |
| PEG 300 | | 0.05 | |
| PEG 400 | | | 0.05 |
| Span 20 | 4.8 | 4.8 | 4.8 |
| Tween 20 | 42.9 | 42.9 | 42.9 |
| Linoleic Acid | 47.6 | 47.6 | 47.6 |
| Acyclovir (mg/ml) | 114 | 114 | 114 |

Each of the above formulations can be used to provide an acyclovir pharmaceutical preparation suitable for oral delivery, using any of the acyclovir forms mentioned herein. The above formulations can be modified to contain acyclovir in concentrations of 1–250 mg acyclovir/ml of vehicle.

The acyclovir transport results observed across Caco-2 cells, using the microemulsions and preparations described in this example in the in vitro procedures described in detail earlier, are graphically illustrated in FIG. 12.

EXAMPLE 12

The following tables list different possible ratios of Pluronic L44/Linoleic acid/Hank's buffer as an emulsion for acyclovir delivery.

TABLE 12

| µE | Pluronic L44 | Linoleic Acid | Aqueous |
|---|---|---|---|
| 12A | 27 | 63.1 | 9.9 |
| 12B | 6 | 90 | 4 |
| 12C | 20 | 40 | 40 |
| 12D | 10 | 10 | 80 |
| 12E | 40 | 50 | 10 |
| 12F | 20 | 70 | 10 |
| 12G | 40 | 30 | 30 |
| 12H | 80 | 10 | 10 |
| 12I | 60 | 10 | 30 |
| 12J | 40 | 10 | 50 |
| 12K | 60 | 30 | 10 |

Each of the above formulations can be used to provide an acyclovir pharmaceutical preparation suitable for oral delivery, using any of the acyclovir forms mentioned herein. The above formulations can be combined with acyclovir in concentrations of 1–250 mg acyclovir/ml of vehicle.

The acyclovir transport results observed across Caco-2 cells, using the microemulsions and preparations described in this example in the in vitro procedures described in detail earlier, are graphically illustrated in FIG. 13.

EXAMPLE 13

The following example lists formulations containing increasing concentration of Acyclovir and gelling agents soluble in the oily phase of the Pluronic L44 microemulsion.

TABLE 13

| Ingredient* | 13A(%) | 13B(%) | 13C(%) |
|---|---|---|---|
| Pluronic L44 | 26.0 | 26.0 | 26.0 |
| Linoleic Acid | 63.1 | 63.1 | 63.1 |
| Aqueous Phase | 9.9 | 9.9 | 9.9 |
| Acyclovir (mg/ml) | 121 | 243 | 495 |

*Each formulation included 1% (w/w).

Each of the above formulations can be used to provide an acyclovir pharmaceutical preparation suitable for oral delivery, using any of the acyclovir forms mentioned herein. The above formulations can be modified to contain acyclovir in concentrations of 1–250 mg acyclovir/ml of vehicle.

The acyclovir transport results observed across Caco-2 cells, using the microemulsions and preparations described in this example in the in vitro procedures described in detail earlier, are graphically illustrated in FIG. 14.

TABLE 14

| Ingredient | 14A(%) | 14B(%) | 14C(%) | 14D(%) | 14E(%) |
|---|---|---|---|---|---|
| Cetearyl Alcohol | 13.3 | | 6.7 | | |
| Myristic Acid | | 11.3 | | | |
| Glycon P-45 | | | | 2.5 | |
| Lauric Acid | | | | | 13.3 |
| Pluronic L44 | 26.7 | 22.6 | 26.7 | 21.6 | 26.7 |
| Linoleic Acid | 48.9 | 52.8 | 55.6 | 62.8 | 48.9 |
| Aqueous Phase | 11.0 | 13.2 | 11.0 | 8.1 | 11.0 |

Each of the above formulations can be used to provide an acyclovir pharmaceutical preparation suitable for oral delivery, using any of the acyclovir forms mentioned herein. The above formulations can be combined with acyclovir in concentrations of 1–500 mg acyclovir/ml of vehicle.

The acyclovir transport results observed across Caco-2 cells, using the microemulsions and preparations described in this example in the in vitro procedures described in detail earlier, are graphically illustrated in FIG. 15.

EXAMPLE 14

The below formulations illustrate the inclusion of a fatty ester material in the Pluronic L44 or Tween 20/Span 20 microemulsions. All of the materials are GRAS or food grade.

TABLE 15

| Ingredient | 15A(%) | 15B(%) | 15C(%) | 15D(%) | 15E(%) |
|---|---|---|---|---|---|
| Myverol 18-99 | 0.9 | 0.95 | | | |
| Myvacet 9-45 | | | 0.9 | 0.95 | |
| Tenox GT-2 | | | | | 0.9 |
| Linoleic Acid | 61.8 | 46.7 | 61.8 | 46.7 | 61.8 |
| Aqueous | 11.8 | 4.7 | 11.8 | 4.7 | 11.8 |
| Tween 20 | | 42.9 | | 42.9 | |
| Span 20 | | 4.75 | | 4.75 | |
| Pluronic L44 | 25.5 | | 25.5 | | 25.5 |

TABLE 16

| Ingredient | 16A(%) | 16B(%) | 16C(%) | 16D(%) | 16E(%) |
|---|---|---|---|---|---|
| Tenox GT-2 | 0.95 | | | | |
| Vitamin E 6-100 | | 0.90 | 0.95 | | |
| Vitamin E TPGS | | | | 8.6 | |
| Myverol 18-99 | | | | | 9.5 |
| Linoleic Acid | 46.7 | 63.1 | 46.7 | 48.6 | 46.6 |
| Aqueous | 4.7 | 9.9 | 4.7 | 18.4 | 4.7 |
| Tween 20 | 42.9 | | 42.9 | | 34.3 |
| Span 20 | 4.75 | | 4.75 | | 4.8 |
| Pluronic L44 | | 26.1 | | 24.5 | |

TABLE 17

| Ingredient | 17A(%) | 17B(%) | 17C(%) | 17D(%) |
|---|---|---|---|---|
| Myverol 18-92 | 0.95 | | | |
| Glycerolmonoricinoleate | | 0.90 | 0.95 | 9.5 |
| Pluronic L44 | | 25.6 | | |
| Tween 20 | 42.9 | | 42.9 | 34.3 |
| Span 20 | 4.76 | | 4.76 | 4.76 |
| Linoleic Acid | 46.7 | 61.7 | 46.7 | 46.7 |
| Aqueous | 4.7 | 11.8 | 4.7 | 4.74 |

TABLE 18

| Ingredient | 18A(%) | 18B(%) | 18C(%) |
|---|---|---|---|
| Aqueous | 9.9 | 4.6 | 4.8 |
| Pluronic L44 | 27 | | |
| Linoleic Acid | 63.1 | 47.7 | 47.7 |
| Tween 20 | | | 42.9 |
| Span 20 | | | 4.8 |
| Labrafac CM10 | | 9.5 | |
| Labrasol | | 38.2 | |

The above formulations illustrate the inclusion of a fatty ester material in the Pluronic L44 or Tween 20/Span 20 microemulsions. All of the materials are GRAS or food grade.

Each of the above formulations can be used to provide an acyclovir pharmaceutical preparation suitable for oral delivery, using any of the acyclovir forms mentioned herein. The above formulations can be combined with acyclovir in concentrations of 1–250 mg acyclovir/ml of vehicle.

Cited Literature

Balfour, Current management of Varicella zoster virus infections. *Journal of Medical Virology*, S1:74–81, 1993.

Barnhart (ed.), *Physicians' Desk Reference*, Oradell, N.J.: Medical Economics Data, 1994.

Elkins et al., Cytomegalovirus disease after heart transplantation: is acyclovir prophylaxis indicated? *Annals Thoracic Surgery*, 56:1267–1273, 1993.

Fletcher et al., Pharmacological basis for high-dose oral acyclovir prophylaxis of cytomegalovirus disease in renal allograft recipients, *Antimicrobial Agents and Chemotherapy*, 35:938–943, 1991.

Griffiths, Current management of cytomegalovirus disease, *Journal of Medical Virology* S1:106–111, 1993.

Katlama, Cytomegalovirus infection in acquired immune deficiency syndrome. *Journal of Medical Virology* S1:128–133, 1993.

McEvoy GK (ed.), *American Hospital Formulary Service*, American Society of Hospital Pharmacists, Inc., Bethesday, Md., 1993.

Mindel, Long-term clinical and psychological management of genital herpes, *Journal of Medical Virology*, S1:39–44, 1993.

O'Brien and Campoli-Richards, Acyclovir: An updated review of its antiviral activity, pharmcokinetic properties and therapeutic effecacy. *Drugs*, 37:233–309, 1989.

Paya et al., Solid organ transplantation: results and implications of acyclovir use in liver transplants, *Journal of Medical Virology* S1:123–127, 1993.

Prentice et al., Impact of long-term acyclovir on cytomegalovirus infection and survival after allogenic bone marrow transplantation. *Lancet* 343:749–753, 1994.

Schaeffer et al., 9-(2-hydroxyethoxymethyl)guanine activity against viruses of the herpes group, *Nature*, 272:583–585, 1978.

Spruance, Prophylactic chemotherapy with acyclovir for recurrent herpes simplex labialis, *Journal of Medical Virology* S1:27–32, 1993.

Stein, et al., The effect of the interaction of acyclovir with zidovudine on progression to AIDS and survival, *Annals of Internal Medicine* 121:100–108, 1994.

What is claimed is:

1. A pharmaceutical composition comprising:
   (a) a water-in-oil emulsion comprising:
      (i) a continuous hydrophobic phase comprising at least one member selected from the group consisting of oleic acid, gadoleic acid, erucic acid, linoleic acid, linolenic acid, ricinoleic acid, arachidonic acid, glyceryl esters of such acids, oleyl alcohol and d-alpha-tocopherol polyethylene glycol succinate;
      (ii) a discontinuous aqueous hydrophilic phase;
      (iii) at least one surfactant for dispersing said hydrophilic phase in said hydrophobic phase as a water-in-oil emulsion, wherein said at least one surfactant includes a member selected from the group consisting of poloxamer 124, a polyglycolized glyceride, sorbitan laurate and polyoxyethylene (20) sorbitan monooleate; and
   (b) acyclovir in said aqueous hydrophilic phase.

2. The composition of claim 1 wherein the hydrophobic phase includes linoleic acid.

3. The composition of claim 1 wherein the hydrophobic phase includes linoleic acid and oleyl alcohol.

4. The composition of claim 1 wherein the hydrophobic phase includes glyceryl behenate in combination with a member selected from the group consisting of oleyl alcohol, oleic acid, glyceryl monooleate, linoleic acid, linolenic acid, ricinoleic acid and mixtures thereof.

5. The composition of claim 1 wherein the hydrophobic phase includes at least one of d-alpha tocopherol polyethylene glycol 1000 succinate.

6. The composition of claim 1 wherein the hydrophobic phase includes at least one of linoleic acid or includes at least one of linoleic acid and linolenic acid and further includes at least one of d-alpha tocopherol polyethylene glycol 1000 succinate or sucrose acetate isobutyrate.

7. The composition of claim 1 wherein at least one of the surfactants includes poloxomer 124.

8. The composition of claim 1 wherein at least one of the surfactants includes a polyglycolized glyceride.

9. The composition of claim 1 wherein at least one of the surfactants includes polyoxyethylene sorbitan monooleate.

10. The composition of claim 1 wherein the surfactant includes polyoxyethylene (20) sorbitan monooleate and sorbitan laurate.

11. The composition of claim 1 wherein the aqueous hydrophilic phase is present in an amount of about 5.1 to about 9.9 weight percent of the emulsion.

12. The composition of claim 1 wherein the aqueous hydrophilic phase includes a water soluble alcohol.

13. The composition of claim 1 wherein the aqueous hydrophilic phase includes a balanced saline solution.

14. The composition of claim 1 wherein the surfactant is present in a range of from about 19 to about 27 weight percent of the emulsion.

15. The composition of claim 1 wherein the hydrophobic phase is present in a range of about 63.1 to about 75.9 weight percent of the emulsion.

16. The composition of claim 1 wherein the emulsion is encapsulated in a capsule comprising an enteric coating material.

17. The composition of claim 16 wherein the enteric coating material is soluble in an acidic aqueous environment.

18. The composition of claim 1 wherein the ester of the hydrophobic phase is a monoglyceryl ester.

* * * * *